US006653128B2

(12) United States Patent
Barbet et al.

(10) Patent No.: US 6,653,128 B2

(45) Date of Patent: Nov. 25, 2003

(54) NUCLEIC ACID VACCINES AGAINST RICKETTSIAL DISEASES AND METHODS OF USE

(75) Inventors: Anthony F. Barbet, Archer, FL (US); Michael V. Bowie, Gainesville, FL (US); Roman Reddy Ganta, Manhattan, KS (US); Michael J. Burridge, Gainesville, FL (US); Suman M. Mahan, Harare (ZW); Travis C. McGuire, Pullman, WA (US); Fred R. Rurangirwa, Pullman, WA (US); Annie L. Moreland, Trenton, FL (US); Bigboy H. Simbi, Harare (ZW); William M. Whitmire, Hamilton, MT (US); Arthur R. Alleman, Alachua, FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 10/062,994

(22) Filed: Jan. 31, 2002

(65) Prior Publication Data

US 2002/0132789 A1 Sep. 19, 2002

Related U.S. Application Data

(60) Division of application No. 09/553,662, filed on Apr. 21, 2000, which is a continuation-in-part of application No. 09/337,827, filed on Jun. 22, 1999, which is a division of application No. 08/953,326, filed on Oct. 17, 1997, now Pat. No. 6,251,872, which is a continuation-in-part of application No. 08/733,230, filed on Oct. 17, 1996, now Pat. No. 6,025,338.

(60) Provisional application No. 60/130,725, filed on Apr. 22, 1999, and provisional application No. 60/269,944, filed on Feb. 20, 2001.

(51) Int. Cl.[7] ........................ C07H 21/04; C12N 15/00; A01N 43/04; A61K 31/70

(52) U.S. Cl. ...................... 435/320.1; 514/44; 530/350; 536/23.7; 935/12; 935/22

(58) Field of Search ..................... 536/23.7; 435/320.1; 514/44; 530/350; 935/12, 22

(56) References Cited

U.S. PATENT DOCUMENTS

| | | | |
|---|---|---|---|
| 4,879,213 | A | 11/1989 | Fox et al. |
| 5,643,578 | A | 7/1997 | Robinson et al. |
| 5,783,441 | A | 7/1998 | Carl et al. |
| 6,025,338 | A | 2/2000 | Barbet et al. |
| 6,251,872 | B1 | 6/2001 | Barbet et al. |

FOREIGN PATENT DOCUMENTS

| | | |
|---|---|---|
| WO | WO 90/12030 | 10/1990 |
| WO | WO 98/16554 | 4/1998 |
| WO | WO 99/13720 | 3/1999 |

OTHER PUBLICATIONS

Bowie, Michael V. et al., "Potential Value of Major Antigenic Protein 2 for Serological Diagnosis of Heartwater and Related Ehrlichial Infections," *Clinical and Diagnostic Immunology*, 1999, 6(2):209–215, Pub: American Society for Microbiology.

Breitschwerdt, Edward B. et al., "Doxycycline Hyclate Treatment of Experimental Canine Ehrlichiosis Followed By Challenge Inoculation with Two *Ehrilichia canis* Strains," *Antimicrobial Agents and Chemotherapy*, 1998, 42(2):362–368, Pub: American Society for Microblology.

Broqui, P. et al., "Serologic Diagnosis of Human Monocytic Enrlichiosis by Immunoblot Analysis," *Clinical & Diagnostic Laboratory Immunology*, 1994, 1(6):645–9, Pub: American Society for Microbiology.

Burgess, Wilson H. et al., "Possible Dissociation of the Heparin–binding and Mitogenic Activities of Heparin–binding (Acidic Fibroblast) Growth Factor–1 from its Receptor–binding Activities by Site–directed Mutagenesis of a Single Lysine Residue," *Journal of Cell Biology*, 1990, 111:2129–2138, Pub: The Rockefeller Univ. Press.

Cox, Graham J.M., et al., "Bovine Herpesvirus 1: Immune Responses in Mice and Cattle Injected with Plasmid DNA," *Journal of Virology*, 1993, 67(9):5664–5667, Pub: American Society for Microbiology.

Danko, I. and J.A. Wolff, "Direct Gene Transfer into Muscle," *Vaccine*, 1994, 12:1499–1553, Pub: Unknown.

Du Plessis, J.L., "Immunity in Heartwater. I. A Preliminary Note on the Role of Serum Antibodies," *Onderstepoort J. vet Res.*, 1970, 37(3):147–150. Pub: Heer Printing Company (Pty) Ltd. for the Govt. Printer, Pretoria, Republic of South Africa.

Dutta, Sukanta K. et al., "Association of Deficiency in Antibody Response to Vaccine and Heterogeneity of *Ehrlichia risticii* Strains with Potomac Horse Fever Vaccine Failure in Horses," *Journal of Clinical Microbiology*, 1998, 36(2):506–512, Pub: American Society for Microbiology.

Goding, J.W., "Production and Application of Monoclonal Antibodies in Cell Biology, Biochemistry & Immunology," *Monoclonal Antibodies: Principles & Practice* (2d ed.), 1986, Ch.3, 78–83, Pub: Academic Press, Harcourt Brace Jovanovich, Publishers, Australia.

Kelly, P.J. et al., "Serological Evidence for Antigenic Relationships Between *Ehrlichia canis* and *Cowdria ruminantium*," Res. Vet. Sci., 1994, 56:170–4, Pub: unknown.

Lazar, Eliane et al., "Transforming Growth Factor α:Mutation of Aspartic Acid 47 and Leucine 48 Results in Different Biological Activities," *Molecular and Cellular Biology*, 1988, 8(3): 1247–1252, Pub: American Society for Microbiology.

(List continued on next page.)

*Primary Examiner*—Patricia A. Duffy

(74) *Attorney, Agent, or Firm*—Saliwanchik, Lloyd & Saliwanchik

(57) ABSTRACT

Described are nucleic acid vaccines containing genes to protect animals or humans against rickettsial diseases. Also described are polypeptides and methods of using these polypeptides to detect antibodies to pathogens.

33 Claims, 8 Drawing Sheets

OTHER PUBLICATIONS

Lewis, Jr., G.E., et al., "Experimentally induced infection of dogs, cats, and nonhuman primates with *Ehrlichia equi*, etiologic agent of equine ehrlichiosis," *Am. J. Vet. Res.*, 1975, 36(1):85–88. (abstract), Pub: Unknown.

Mahan, S.M., et al., "Molecular cloning of a gene encoding the immunogenic 21 kDa protein of *Cowdria ruminantium*," Microbiology, 1994, 140:2135–2142, Pub: Unknown.

McGuire, Travis C., et al., "Recombinant Vaccinia Virus Expression of *Anaplasma marginale* Surface Protein MSP–1a: Effect of Promoters, Leader Sequences and GPI Anchor Sequence on Antibody Response," *Vaccine*, 1994, 12(5):465–471, Pub: Butterworth–Heinemann Ltd.

Nyika, A. et al., "A DNA Vaccine Protects Mice Against the Rickettesial Agent *Cowdria ruminantium*," *Parasite Immunology*, 1998, 20:111–119, Pub: Blackwell Science Ltd.

Oberle, Suzan M. and Anthony F. Barbet, "Derivation of the Complete msp4 Gene Sequence of *Anaplasma marginale* Without Cloning," *Gene*, 1993, 136:291–294, Pub: Elsevier Science Publishers B.V.

Reddy, G. Roman, et al., "Sequence Heterogeneity of the Major Antigenic Protein 1 Genes from *Cowdria ruminantium* Isolates from Different Geographical Areas," Clinical & Diagnostic Laboratory Immunology, 1996, 3(4):417–422, Pub: American Society for Microbiology.

Rikihisa, Y., et al., "Western Immunoblot Analysis of *Ehrlichia chafeensis*, *E. Canis*, or *E. ewingii* Infections in Dogs and Humans," *J. Clin. Microbiology*, 1994, 32(9):2107–12, Pub: American Society for Microbiology.

Rurangirwa, Fred R., et al., "Restriction of Major Surface Protein 2 (MSP2) Variants During Tick Transmission of the Ehrlichia *Anaplama marginale*," *Proc. Natl. Acad. Sci. USA*, 1999, 96:3171–3176 (abstract), Pub: Unknown.

Schodel, M.–T. Aguado and P.–H. Lambert, "Introduction: Nucleic Acid Vaccines, WHO, Geneva, May 17–18, 1994," *Vaccine*, 1994, 12(16):1491–1492, Pub: Butterworth–Heinemann Ltd., Switzerland.

Sedegah, Martha, et al., "Protection Against Malaria by Immunization with Plasmid DNA Encoding Circumsporozoite Protein," *Proc. Natl. Acad. Sci. USA*, 1994, 91:9866–9870, Pub: Unknown.

Sumner, John W., et al., "Protection of Guinea–Pigs from Experimental Rocky Mountain Spotted Fever by Immunization with Baculovirus–Expressed *Rickettsia rickettsii* rOmpA Protein," *Vaccine*, 1995, 13(1):29–35, Pub: Elsevier Science Ltd., Great Britain.

Uilenberg, Gerrit, "Heartwater (*Cowdria ruminantium* infection): Current Status," *Advances In Veterinary Science and Comparative Medicine*, 1983, 27:427–480, Pub: Academic Press, Inc.

Ulmer, J.B. et al., "Heterologous Protection Against Influenza by Injection of DNA Encoding a Viral Protein," *Science*, 1993, 259:1745–1749, Pub: Unknown.

Ulmer, Jeffrey B. et al., "DNA Vaccines Promising: A New Approach to Inducing Protective Immunity," *ASM News*, 1996, 62(9):476–479, Pub: American Society for Microbiology.

van Vliet, A.H.M. et al., "Molecular Cloning, Sequence Analysis, and Expression of the Gene Encoding the Immunodominant 32–Kilodalton Protein of *Cowdria ruminantium*," *Infection & Immunity*, 1994, 62(4):1451–6, Pub: Unknown.

Van Vliet, A.H.M., et al., "Use of a Specific Immunogenic Region on the *Cowdria ruminantium* MAP1 Protein in a Serological Assay," *J. Clinical Microbiology*, 1995, 33(9):2405–10, Pub: American Society of Microbiology.

Vemulapalli, R. et al., "Pathogenic, Immunologic, and Molecular Differences Between Two *Ehrlichia ristici* Strains," *J. Clinical Microbiology*, 1995, 33(11):2987–2993, Pub: American Society for Microbiology.

Vishwanath, Suryanarayanan, et al., "A Recombinant *Reckettsia conoril* Vaccine Protects Guinea Pigs from Experimental Boutonneuse Fever and Rocky Mountain Spotted Fever," *Infection and Immunity*, 1990, 58(3):646–653

FIG. 1A

```
C.r.   ATGAATTGCAAGAAAATTTTTA------------TCACAAGTACACTAATATCATTAGTG
E.c.   ATGAATTACAAAAAAAGTTTCA-------------TAACAGCG-ATTGATATCATTAATA
A.m.   ATGAATTACAGAGAATTGTTTACAGGGGGCCTG-TCAGCAGCC-ACAGTCTGCGCCTGCT
       ******* **   **   ** *              *  **   *       *

C.r.   TCATTTT--TACCTGGTGTGTCCTTTTCTGATGTAATACAGGAAGACAGCAACCCAGCAG
E.c.   TCCTTCTCTTACCTGGAGTATCATTTTCCGACCCAAGGCAGGTAGTGGTCA---TTAACG
A.m.   CCCTACTTGTTAGTGGGGCCGTAGTGGCATCTCCCATGAGTCACGAAGTGGCTTCTGAAG
        * *  *  *   *** *      *  *       *        *              *

C.r.   GCAGTGTTTACATTAGCGCAAAATACATGCCAACTGCATCACATTTTGGTAAAATGTCAA
E.c.   GTAATTTCTACATCAGTGGAAAATACGATGCCAAGGCTTCGCATTTTGGAGTATTCTCTG
A.m.   GGGGAGTAATGGGAGGTAGCTTTTACGTGGGTGCGGCCT-ACAGCCCAGCATTTCCTTCT
       *     *        *       ***         ** *  **     *       *

C.r.   TCAAAGAAGATTCAAAAAATACTCAAACGGTATTTGGTCTAAAAAAAGATTGGGATGGCG
E.c.   CTAAGGAAGAAAGAAATACAACAGTTGGAGTGTTTGGACTGAAGCAAAATTGGGACGGAA
A.m.   GTTACCTCGTTCGACATGCGTGAGTCAAGCAAAGAGACCTCA--TACGTTAGAGGCTATG
          *    *    * *                   *  ** *   *   * * *

C.r.   TTAAAACACCATCAGATTCTAGCAATACTAATTCTACAATTTTTACTGAAAAAGACTATT
E.c.   GCGCAATATC--CAACTCCTCCCCAAACGA-------TGTATTCACTGTCTCAAATTATT
A.m.   ACAAGAGCATTGCAACGATTGATGTGAGTGTGCCAGCAAACTTTTCCAAATCTGGCTACA
            *      **     *      *              **  *          **

C.r.   CTTTCAGATATGAAAACAATCCGTTTTTAGGTTTCGCTGGAGCAATTGGGTACTCAATGA
E.c.   CATTTAAATATGAAAACAACCCGTTTTTAGGTTTTGCAGGAGCTATTGGTTACTCAATGG
A.m.   CTTTTGCCTTCTCTAAAAACTTAATCACGTCTTTCGACGGCGCTGTGGGATATTCTCTGG
       * **    *     ** **     *      *** *  ** **  * ** ** **  **
```

FIG. 1B

```
C.r.    ATGGACCAAGAATAGAGTTCGAAGTATCCTATGAAACTTTTGATGTAAAAAACCTAGGTG
E.c.    ATGGTCCAAGAATAGAGCTTGAAGTATCTTATGAAACATTTGATGTAAAAAATCAAGGTA
A.m.    GAGGAGCCAGAGTGGAATTGGAAGCGAGCTACAGAAGGTTTGCTACTTTGGCGGACGGGC
          **  * *** * **  * ****     **   **  **** *             **

C.r.    GCAACTATAAAAACAACGCACACATGTACTGTGCTTTAGATACAGCAGCACAAAATAGCA
E.c.    ACAATTATAAGAATGAAGCACATAGATATTGTGCTCTATCCCATAACTCAGCAGCAGACA
A.m.    AGTACGCAAAAAGTG---------------GTGCGGAATCTCTGGCAGCTATTACCCGCG
           *    ** *                  ****   *          *         *

C.r.    CTAATGGCGCAGGATTAACTACATCTGTTATGGTAAAAAACGAAAATTTAACAAATATAT
E.c.    TGAGTAGTGCAAG---TAATAATTTTGTCTTTCTAAAAAATGAAGGATTACTTGACATAT
A.m.    ACGCTAACATTACTGAGACCAATTACTTCGTAGTCAAAATTGATGAAATCACAAACACCT
            *            *  *  *   *  *  * ****  **     *     * *  *

C.r.    CATTAATGTTAAATGCGTGTTATGATATCATGCTTGATGGAATACCAGTTTCTCCATATG
E.c.    CATTTATGCTGAACGCATGCTATGACGTAGTAGGCGAAGGCATACCTTTTTCTCCTTATA
A.m.    CAGTCATGTTAAATGGCTGCTATGACGTGCTGCACACAGATTTACCTGTGTCCCCGTATG
        ** * *** * ** *  ** *****  *  *       *   ****  * ** ** ***

C.r.    TATGTGCAGGTATTGGCACTGACTTAGTGTCAGTAATTAATGCTACAAATCCTAAATTAT
E.c.    TATGCGCAGGTATCGGTACTGATTTAGTATCCATGTTTGAAGCTACAAATCCTAAAATTT
A.m.    TATGTGCCGGGATAGGCGCAAGCTTTGTTGACATCTCTAAGCAAGTAACCACAAAGCTGG
        **** ** ** ** **  *    ** **     *   * *      **    * **  *

C.r.    CTTATCAAGGAAAGCTAGGCATAAGTTACTCAATCAATTCTGAAGCTTCTATCTTTATCG
E.c.    CTTACCAAGGAAAGTTAGGTTTAAGCTACTCTATAAGCCCAGAAGCTTCTGTGTTTATTG
A.m.    CCTACAGGGGCAAGGTTGGGATTAGCTACCAGTTTACTCCGGAAATATCCTTGGTGGCAG
        * **    ** *** * **  * ** ***    * *   * ***   **  *  *    *
```

FIG. 1C

```
C.r.   GTGGACATTTCCATAGAGTTATAGGTAATGAATTTAAAGATATTGCTACCTTAAAAATAT
E.c.   GTGGGCACTTTCATAAGGTAATAGGGAACGAATTTAGAGATATTCCTACTATAATACCTA
A.m.   GTGGGTTCTACCACGGGCTATTTGATGAGTCTTACAAGGACATTCCCGCACACAACAGTG
       ****    *  **     *  * *   *    *  *  ** *** *  *    *

C.r.   TTACTTCAAAAACAGGAATATCTAATCCTGGCTTTGCATCAGCAACACTTGATGTTTGTC
E.c.   CTGGATCAACACTTGCAGGAAAAGGAAACTACCCTGCAATAGTAATACTGGATGTATGCC
A.m.   TAAAGTTCTCTGGAGAAGCAAAA------------GCCTCAGTCAAAGCGCATATTGCTG
            *        * *  *               **   **  * *    ** *

C.r.   ACTTTGGTATAGAAATTGGAGGAAGGTTTGTATTTTAA---
E.c.   ACTTTGGAATAGAAATGGGAGGAAGGTTTAA----------
A.m.   ACTACGGCTTTAACCTTGGAGCAAGATTCCTGTTCAGCTAA
       ***  **  *  *  * **** *** **
```

```
   1 ggaatgaattcagggacatttctactcttaaagcgtttgctacaccatcatctgcagcta
       N  E  F  R  D  I  S  T  L  K  A  F  A  T  P  S  S  A  A  T
  61 ctccagacttagcaacagtaacactgagtgtgtgtcactttggagtagaacttggaggaa
       P  D  L  A  T  V  T  L  S  V  C  H  F  G  V  E  L  G  G  R
 121 gatttaacttctaattttattattgccacatgttaaaaataatctaaacttgttttcatt
       F  N  F  *
 181 attgctacaaataaataaaatagtggcaaaaaaatgtagcaataagagggggggggggga
 241 ctaattactatctgccatatcccttactaccacttacactaaataatctgacaaatacaa
 301 cagcttctggagaaataaacaatatttaaatttttcttacaaaaaccatttatatcttgt
                                                      -35
 361 actaaaaactagcttataacttgtttttacattgtaggtttactactgttaatttgtttt
                     -10
 421 cactatttcaggtgtaatatgaactgcgaaaaatttttataacaactgcattaacatta
                RBS      M  N  C  E  K  F  F  I  T  T  A  L  T  L
 481 ctaatgtccttcttacctggaatatcactttctgatccagtacaggatgacaacattagt
     L  M  S  F  L  P  G  I  S  L  S  D  P  V  Q  D  D  N  I  S
 541 ggtaatttctacatcagtggaaagtatatgccaagcgcttcgcatttggagtttttct
     G  N  F  Y  I  S  G  K  Y  M  P  S  A  S  H  F  G  V  F  S
 601 gccaaggaagaaagaaatacaacagttggagtatttggaatagagcaagattgggataga
     A  K  E  E  R  N  T  T  V  G  V  F  G  I  E  Q  D  W  D  R
 661 tgtgtaatatctagaaccactttaagcgatatattcaccgttccaaattattcatttaag
     C  V  I  S  R  T  T  L  S  D  I  F  T  V  P  N  Y  S  F  K
 721 tatgaaaataatctattttcaggatttgcaggagctattggctactcaatggatggccca
     Y  E  N  N  L  F  S  G  F  A  G  A  I  G  Y  S  M  D  G  P
 781 agaatagagcttgaagtatctTatgaagcattcgatgttaaaaatcaaggtaacaattat
     R  I  E  L  E  V  S  Y  E  A  F  D  V  K  N  Q  G  N  N  Y
 841 aagaacgaagcacatagatattatgctctgtcccatcttctcggcacagagacacagata
     K  N  E  A  H  R  Y  Y  A  L  S  H  L  L  G  T  E  T  Q  I
 901 gatggtgcaggcagtgcgtctgtctttctaataaatgaaggactacttgataaatcattt
     D  G  A  G  S  A  S  V  F  L  I  N  E  G  L  L  D  K  S  F
 961 atgctgaacgcatgttatgatgtaataagtgaaggcatacctttttctccttatatatgt
     M  L  N  A  C  Y  D  V  I  S  E  G  I  P  F  S  P  Y  I  C
1021 gcaggtattggtattgatttagtatccatgtttgaagctataaatcctaaaatttcttat
     A  G  I  G  I  D  L  V  S  M  F  E  A  I  N  P  K  I  S  Y
1081 caaggaaaattaggcttaagttaccctataagcccagaagcttctgtgtttattggtgga
     Q  G  K  L  G  L  S  Y  P  I  S  P  E  A  S  V  F  I  G  G
1141 cattttcataaggtgataggaaacgaatttagagatattcctactatgatacctagtgaa
     H  F  H  K  V  I  G  N  E  F  R  D  I  P  T  M  I  P  S  E
1201 tcagcgcttgcaggaaaaggaaactaccctgcaatagtaacactggacgtgttctacttt
     S  A  L  A  G  K  G  N  Y  P  A  I  V  T  L  D  V  F  Y  F
1261 ggcatagaacttggaggaaggtttaacttccaactttgattattgccacaataaataaaa
     G  I  E  L  G  G  R  F  N  F  Q  L  *
1321 atagtggcaaaagaatgtagcaataagagggggagggggaactaaattattatttgcc
1381 atatcccttactaccacttacaccaaataatctgacaaatacaacagttcaaacaaaggt
1441 aaacaattcttaaatttgtcttatgagaaccattgatatcttatattaaaaactagctta
                                          -35
1501 taacttgtctttacattgcagttctactattgttaatttattttcactattttaggtgta
     -10                                                  RBS
1561 atatgaattgcaaaaaatttttataacaactgcattagtatcactaatgtcctttctac
       M  N  C  K  K  F  F  I  T  T  A  L  V  S  L  M  S  F  L  P
1621 ctggaatatcattttctgatccagtgcaaggtgacaatattagtggtaatttctatgtta
       G  I  S  F  S  D  P  V  Q  G  D  N  I  S  G  N  F  Y  V  S
1681 gtggcaagtatatgccaagtgcttcgcatttggcatgttttctgccaaagaagaaaaaa
       G  K  Y  M  P  S  A  S  H  F  G  M  F  S  A  K  E  E  K  N
1741 atcctactgttgcattgtatggcttaaaacaagattgggaagggattagctcatcaagtc
       P  T  V  A  L  Y  G  L  K  Q  D  W  E  G  I  S  S  S  S  H
1801 acaatgataatcatttcaataacaagggttattcatttaaatatgaaaataacccatttt
       N  D  N  H  F  N  N  K  G  Y  S  F  K  Y  E  N  N  P  F  L
1861 tagggtttgcaggagctattggttattcaatgggtggtccaagagtagagtttgaagtgt
       G  F  A  G  A  I  G  Y  S  M  G  G  P  R  V  E  F  E  V  S
1921 cctatgaaacatttgacgttaaaaatcagggtaataactataaaaatgatgctcacagat
       Y  E  T  F  D  V  K  N  Q  G  N  N  Y  K  N  D  A  H  R  Y
1981 actgtgctttaggtcaacaagacaacagcggaatacctaaaactagtaaatacgtactgt
       C  A  L  G  Q  Q  D  N  S  G  I  P  K  T  S  K  Y  V  L  L
2041 taaaaagcgaaggattgcttgacatatcatttatgctaaatgcatgctatgatataataa
       K  S  E  G  L  L  D  I  S  F  M  L  N  A  C  Y  D  I  I  N
2101 acgagagcatacctttgtctccttacatatgtgcaggtgttggtActgatttaatatcca
       E  S  I  P  L  S  P  Y  I  C  A  G  V  G  T  D  L  I  S  M
2161 tgtttgaagctacaaatcctaaaatttcttaccaagggaagttaggtctaagttactcta
       F  E  A  T  N  P  K  I  S  Y  Q  G  K  L  G  L  S  Y  S  I
2221 taaacccagaagcttctgtatttattggtggacattttcataaggtgataggaaacgaat
       N  P  E  A  S  V  F  I  G  G  H  F  H  K  V  I  G  N  E  F
2281 ttagggacattcctactctgaaagcatttgttacgtcatcagctactccagatctagcaa
       R  D  I  P  T  L  K  A  F  V  T  S  S  A  T  P  D  L  A  I
```

FIG. 2A

```
2341 tagtaacactaagtgtatgtcattttggaatagaacttggaggaaggtttaacttctaat
       V  T  L  S  V  C  H  F  G  I  E  L  G  G  R  F  N  F  *
2401 tttgttattgccacatgttaaaaataatctaaacttgttttcattattgctacagtaaat
2461 aaaaatagtggcaaaagaatgtagcaataagaaggggggggggggactaaattgctattt
2521 accatatcccttattataccacttacactaaataacttgacaaatacaacagcttctgga
2581 aaaacaaacaatacttaaatttctcttacaaaaaccatttatatcttgtactaaaaacta
                                               -35
2641 gcttataacttgtttttacattgtagttctactattgttaatttattttcactattttag
         -10
2701 gtgcaatatgaattgcaaaaaatttttataacaactacattagtatcgctaatgtcctt
     RBS    M  N  C  K  K  F  F  I  T  T  T  L  V  S  L  M  S  F
2761 cttacctggaatatcatttctgatgcagtacagaacgacaatgttggtggtaatttcta
       L  P  G  I  S  F  S  D  A  V  Q  N  D  N  V  G  G  N  F  Y
2821 tatcagtgggaaatatgtaccaagtgtttcacatttggcgtattctctgctaaacagga
       I  S  G  K  Y  V  P  S  V  S  H  F  G  V  F  S  A  K  Q  E
2881 aagaaatacaacaatcggagtatttggattaaagcaagattgggatggcagcacaatatc
       R  N  T  T  I  G  V  F  G  L  K  Q  D  W  D  G  S  T  I  S
2941 taaaaattctccagaaaatacatttaacgttccaaattattcatttaaatatgaaaataa
       K  N  S  P  E  N  T  F  N  V  P  N  Y  S  F  K  Y  E  N  N
3001 tccatttctaggttttgcaggagctgttggttatttaatgaatggtccaagaatagagtt
       P  F  L  G  F  A  G  A  V  G  Y  L  M  N  G  P  R  I  E  L
3061 agaaatgtcctatgaaacatttgatgtgaaaaaccagggtaataactataagaacgatgc
       E  M  S  Y  E  T  F  D  V  K  N  Q  G  N  N  Y  K  N  D  A
3121 tcacaaatattatgctttaacccataacagtggggaaagctaagcaatgcaggtgataa
       H  K  Y  Y  A  L  T  H  N  S  G  G  K  L  S  N  A  G  D  K
3181 gtttgtttttctaaaaaatgaaggactacttgatatatcacttatgttgaatgcatgcta
       F  V  F  L  K  N  E  G  L  L  D  I  S  L  M  L  N  A  C  Y
3241 tgatgtaataagtgaaggaatacctttctctccttacatatgtgcaggtgttggtactga
       D  V  I  S  E  G  I  P  F  S  P  Y  I  C  A  G  V  G  T  D
3301 tttaatatccatgtttgaagctataaaccctaaaatttcttatcaaggaaagttaggttt
       L  I  S  M  F  E  A  I  N  P  K  I  S  Y  Q  G  K  L  G  L
3361 gagttactccataagcccagaagcttctgtttttgttggtggacattttcataaggtgat
       S  Y  S  I  S  P  E  A  S  V  F  V  G  G  H  F  H  K  V  I
3421 agggaatgaattcagagatattcctgctatgatacccagtacctcaactctcacaggtaa
       G  N  E  F  R  D  I  P  A  M  I  P  S  T  S  T  L  T  G  N
3481 tcactttactatagtaacactaagtgtatgccactttggagtggaacttggaggaaggtt
       H  F  T  I  V  T  L  S  V  C  H  F  G  V  E  L  G  G  R  F
3541 taacttttaattttattattgccacatgttaaaaataatctaaacttgtttttattattg
       N  F  *
3601 ctgcaggtaaataaaaatagtggcaaaagaatgtagcaataagagggggggggggactag
3661 tttataagtgctgtttttctcacctttacacatgatactatacttaaccagtttttttgc
3721 tattacttacctgacgtaatatattaaatttccttacaaaagttaccgatattttatac
                                                       -35
3781 aaaaatttatattctgacttgcttttatatgacacttctactattgttaatttatttgtc
             -10
3841 actattaggttatatatgaattacaaaaaagttttcataacaagtgcattgatatcatta
             RBS      M  N  Y  K  K  V  F  I  T  S  A  L  I  S  L
3901 atatcttctctacctggagtatcattttccgacccagcaggtagtggtattaacggtaat
     I  S  S  L  P  G  V  S  F  S  D  P  A  G  S  G  I  N  G  N
3961 ttctacatcagtggaaaatacatgccaagtgcttcgcatttggagtattctctgctaag
     F  Y  I  S  G  K  Y  M  P  S  A  S  H  F  G  V  F  S  A  K
4021 gaagaaagaaatacaacagttggagtgtttggactgaagcaaaattgggacggaagcgca
     E  E  R  N  T  T  V  G  V  F  G  L  K  Q  N  W  D  G  S  A
4081 atatccaactcctccccaaacgatgtattcactgtctcaaattattcatttaaatatgaa
     I  S  N  S  S  P  N  D  V  F  T  V  S  N  Y  S  F  K  Y  E
4141 aacaacccgtttttaggttttgcaggagctattggttactcaatggatggtccaagaata
     N  N  P  F  L  G  F  A  G  A  I  G  Y  S  M  D  G  P  R  I
4201 gagcttgaagtatcttatgaaacatttgatgtaaaaaatcaaggtaacaattataagaat
     E  L  E  V  S  Y  E  T  F  D  V  K  N  Q  G  N  N  Y  K  N
4261 gaagcacatagatattgtgctctatcccataactcagcagcagacatgagtagtgcaagt
     E  A  H  R  Y  C  A  L  S  H  N  S  A  A  D  M  S  S  A  S
4321 aataatttgtctttctaaaaaatgaaggattacttgacatatcatttatgctgaacgca
     N  N  F  V  F  L  K  N  E  G  L  L  D  I  S  F  M  L  N  A
4381 tgctatgacgtagtaggcgaaggcatacctttttctccttatatatgcgcaggtatcggt
     C  Y  D  V  V  G  E  G  I  P  F  S  P  Y  I  C  A  G  I  G
4441 actgatttagtatccatgtttgaagctacaaatcctaaaatttcttaccaaggaaagtta
     T  D  L  V  S  M  F  E  A  T  N  P  K  I  S  Y  Q  G  K  L
4501 ggtttaagctactctataagcccagaagcttctgtgtttattggtgggcactttcataag
     G  L  S  Y  S  I  S  P  E  A  S  V  F  I  G  G  H  F  H  K
4561 gtaatagggaacgaatttagagatattcctactataatacctactggatcaacacttgca
     V  I  G  N  E  F  R  D  I  P  T  I  I  P  T  G  S  T  L  A
4621 ggaaaaggaaactaccctgcaatagtaatactggatgtatgccactttggaatagaaatg
     G  K  G  N  Y  P  A  I  V  I  L  D  V  C  H  F  G  I  E  M
4681 gga

     G
```

```
   1 tggtgtaaatatgaaatataaaaaactttacagtaactgcattagtattattaacttc
      RBS       M  K  Y  K  K  T  F  T  V  T  A  L  V  L  L  T  S
  61 ctttacacattttataccttttatagtccagcacgtgccagtacaattcacaacttcta
      F  T  H  F  I  P  F  Y  S  P  A  R  A  S  T  I  H  N  F  Y
 121 cattagtggaaaatatatgccaacagcgtcacattttggaatttttcagctaaagaaga
      I  S  G  K  Y  M  P  T  A  S  H  F  G  I  F  S  A  K  E  E
 181 acaaagttttactaaggtattagttgggttagatcaacgattatcacataatattataaa
      Q  S  F  T  K  V  L  V  G  L  D  Q  R  L  S  H  N  I  I  N
 241 caataatgatacagcaaagagtcttaaggttcaaaattattcatttaaatacaaaaataa
      N  N  D  T  A  K  S  L  K  V  Q  N  Y  S  F  K  Y  K  N  N
 301 cccatttctaggatttgcaggagctattggttattcaataggcaattcaagaatagaact
      P  F  L  G  F  A  G  A  I  G  Y  S  I  G  N  S  R  I  E  L
 361 agaagtatcacatgaaatatttgatactaaaaacccaggaaacaattatttaaatgactc
      E  V  S  H  E  I  F  D  T  K  N  P  G  N  N  Y  L  N  D  S
 421 tcacaaatattgcgctttatctcatggaagtcacatatgcagtgatggaaatagcggaga
      H  K  Y  C  A  L  S  H  G  S  H  I  C  S  D  G  N  S  G  D
 481 ttggtacactgcaaaaactgataagtttgtacttctgaaaaatgaaggtttacttgacgt
      W  Y  T  A  K  T  D  K  F  V  L  L  K  N  E  G  L  L  D  V
 541 ctcatttatgttaaacgcatgttatgacataacaactgaaaaaatgccttttttcacctta
      S  F  M  L  N  A  C  Y  D  I  T  T  E  K  M  P  F  S  P  Y
 601 tatatgtgcaggtattggtactgatctcatatctatgtttgagacaacacaaaacaaaat
      I  C  A  G  I  G  T  D  L  I  S  M  F  E  T  T  Q  N  K  I
 661 atcttatcaaggaaagttaggtttaaactatactataaactcaagagtttctgtttttgc
      S  Y  Q  G  K  L  G  L  N  Y  T  I  N  S  R  V  S  V  F  A
 721 aggtgggcactttcataaggtaataggtaatgaatttaaaggtattcctactctattacc
      G  G  H  F  H  K  V  I  G  N  E  F  K  G  I  P  T  L  L  P
 781 tgatggatcaaacattaaagtacaacagtctgcaacagtaacattagatgtgtgccattt
      D  G  S  N  I  K  V  Q  Q  S  A  T  V  T  L  D  V  C  H  F
 841 cgggttagagattggaagtagatttttcttttaatacttctattgtacatgttaaaaata
      G  L  E  I  G  S  R  F  F  F  *
 901 gtactagtttgcttctgtggtttataaacgcaagagagaaatagttagtaataaattaga
 961 aagttaaatattagaaaagtcatatgtttttcattgtcattgatactcaactaaaagtag
1021 tataaatgttacttattaataattttacgtagtatattaaatttcccttacaaaagccac
1081 tagtatttatactaaaagctatacttggcttgtatttaatttgtatttttactactgt
      -35                    -10
1141 taatttactttcactgtttctggtgtaaatatgaattgtaaaaaagttttcacaataagt
                           RBS       M  N  C  K  K  V  F  T  I  S
1201 gcattgatatcatccatatacttcctacctaatgtctcatactctaacccagtatatggt
     A  L  I  S  S  I  Y  F  L  P  N  V  S  Y  S  N  P  V  Y  G
1261 aacagtatgtatggtaatttttacatatcaggaaagtacatgccaagtgttcctcatttt
     N  S  M  Y  G  N  F  Y  I  S  G  K  Y  M  P  S  V  P  H  F
1321 ggaatttttcagctgaagaagagaaaaaaaagacaactgtagtatatggcttaaaagaa
     G  I  F  S  A  E  E  E  K  K  K  T  T  V  V  Y  G  L  K  E
1381 aactgggcaggagatgcaatatctagtcaaagtccagatgataattttaccattcgaaat
     N  W  A  G  D  A  I  S  S  Q  S  P  D  D  N  F  T  I  R  N
1441 tactcattcaagtatgcaagcaacaagtttttagggtttgcagtagctattggttactcg
     Y  S  F  K  Y  A  S  N  K  F  L  G  F  A  V  A  I  G  Y  S
1501 ataggcagtccaagaatagaagttgagatgtcttatgaagcatttgatgtaaaaaatcaa
     I  G  S  P  R  I  E  V  E  M  S  Y  E  A  F  D  V  K  N  Q
1561 ggtaacaatt
     G  N  N
```

FIG. 2C

```
1     acatgtatacattatagtaacaaatgttaccgtattttattcataagttaagtaaaatct

61    ataccattctctttcactttatcagaagacttttatttatcacaaactcatgacgtatag

121   tgtcacaaataaacacactgcaactgcaatcactacgtaaaactttaactcttcttttc

181   acaactaaaatactaataaaagtaatatagtataaaaaatcttaagtaacTTGACAtaat
                                                         -35
241   attactctgataTAGCATatgtctagtatctctatactaaacgtttatataattGGAGca
                  -10
301   tattaATGAAAGCTATCAAATTCATACTTAATGTCTGCTTACTATTTGCAGCAATATTTT
           M  K  A  I  K  F  I  L  N  V  C  L  L  F  A→ A  I  F  L

361   TAGGGTATTCCTATATTACAAAACAAGGCATATTTCAAACAAAACATCATGATACACCTA
        G  Y  S  Y  I  T  K  Q  G  I  F  Q  T  K  H  H  D  T  P  N

421   ATACTACTATACCAAATGAAGACGGTATTCAATCTAGCTTTAGCTTAATCAATCAAGACG
        T  T  I  P  N  E  D  G  I  Q  S  S  F  S  L  I  N  Q  D  G

481   GTAAAACAGTAACCAGCCAAGATTTCCTAGGGAAACACATGTTAGTTTTGTTTGGATTCT
        K  T  V  T  S  Q  D  F  L  G  K  H  M  L  V  L  F  G  F  S

541   CTGCATGTAAAAGCATTTGCCCTGCAGAATTGGGATTAGTATCTGAAGCACTTGCACAAC
        A  C  K  S  I  C  P  A  E  L  G  L  V  S  E  A  L  A  Q  L

601   TTGGTAATAATGCAGACAAATTACAAGTAATTTTTATTACAATTGATCCAAAAAATGATA
        G  N  N  A  D  K  L  Q  V  I  F  I  T  I  D  P  K  N  D  T

661   CTGTAGAAAAATTAAAAGAATTTCATGAACATTTTGATTCAAGAATTCAAATGTTAACAG
        V  E  K  L  K  E  F  H  E  H  F  D  S  R  I  Q  M  L  T  G

721   GAAATACTGAAGACATTAATCAAATAATTAAAAATTATAAAATATATGTTGGACAAGCAG
        N  T  E  D  I  N  Q  I  I  K  N  Y  K  I  Y  V  G  Q  A  D

781   ATAAAGATCATCAAATTAACCATTCTGCAATAATGTACCTTATTGACAAAAAAGGATCAT
        K  D  H  Q  I  N  H  S  A  I  M  Y  L  I  D  K  K  G  S  Y

841   ATCTTTCACACTTCATTCCAGATTTAAAATCACAAGAAAATCAAGTAGATAAGTTACTAT
        L  S  H  F  I  P  D  L  K  S  Q  E  N  Q  V  D  K  L  L  S

901   CTTTAGTTAAGCAGTATCTGTAAtttaataattaattAAAGagaatagtacacaCTTTtt
        L  V  K  Q  Y  L  *

961   ataaattcatggaatacgttggatgagtaggtttttttagtatttttagtgctaataac
1021  attggcat
```

FIG. 3A

```
   1  ggaaatctcatgtaaacgtgaaatactatattctttttaaataccaatacaattgaata

  61  caaaaaaacttttacaacttattatgtttatcttaaaccttattttaagattccttatg

 121  tcacaaaataacaaaaatactatttacaaaatacaccacaatttcatcaaataaaaaaa

 181  ctatacactttattatactacagtagatataccataaaagattttaagtaacTTGACAta
                                                          -35
 241  atattaccttggtaTAGCATatgattcagtattttatattaaatttattatgtattGGA
                   -10
 301  GcataaaATGAAAGTTATCAAATTTATACTTAATATCTGTTTATTATTTGCAGCAATTTT
              M  K  V  I  K  F  I  L  N  I  C  L  L  F  A →A  I  F

 361  TCTAGGATATTCCTACGTAACAAAACAAGGCATTTTTCAAGTAAGAGATCATAACACTCC
       L  G  Y  S  Y  V  T  K  Q  G  I  F  Q  V  R  D  H  N  T  P

 421  CAATACAAATATATCAAATAAAGCCAGCATTACTACTAGTTTTTCGTTAGTAAATCAAGA
       N  T  N  I  S  N  K  A  S  I  T  T  S  F  S  L  V  N  Q  D

 481  TGGAAATACAGTAAATAGTCAAGATTTTTTGGGAAAATACATGCTAGTTTTATTTGGATT
       G  N  T  V  N  S  Q  D  F  L  G  K  Y  M  L  V  L  F  G  F

 541  TTCTTCATGTAAAAGCATCTGCCCTGCTGAATTAGGAATAGCATCTGAAGTTCTCTCACA
       S  S  C  K  S  I  C  P  A  E  L  G  I  A  S  E  V  L  S  Q

 601  GCTTGGTAATGACACAGACAAGTTACAAGTAATTTTCATTACAATTGATCCAACAAATGA
       L  G  N  D  T  D  K  L  Q  V  I  F  I  T  I  D  P  T  N  D

 661  TACTGTACAAAAATTAAAAACATTTCATGAACATTTTGATCCTAGAATTCAAATGCTAAC
       T  V  Q  K  L  K  T  F  H  E  H  F  D  P  R  I  Q  M  L  T

 721  AGGCAGTGCAGAAGATATTGAAAAAATAATAAAAAATTACAAAATATATGTTGGACAAGC
       G  S  A  E  D  I  E  K  I  I  K  N  Y  K  I  Y  V  G  Q  A

 781  AGATAAAGATAATCAAATTGATCACTCTGCCATAATGTACATTATCGATAAAAAAGGAGA
       D  K  D  N  Q  I  D  H  S  A  I  M  Y  I  I  D  K  K  G  E

 841  ATACATTTCACACTTTTCTCCAGATTTAAAATCAACAGAAAATCAAGTAGATAAGTTACT
       Y  I  S  H  F  S  P  D  L  K  S  T  E  N  Q  V  D  K  L  L

 901  ATCTATAATAAAACAATATCTCTAAtttaataattaattaAAGAGaatagtacacaCTCT
        S  I  I  K  Q  Y  L  *

 961  Tatataaattcatggatatatgtgatgggtagatttcttttggtgtttctatcgctaatt
1021  acatta
```

FIG. 3B

NUCLEIC ACID VACCINES AGAINST RICKETTSIAL DISEASES AND METHODS OF USE

CROSS-REFERENCE TO RELATED APPLICATIONS

This application is a divisional of Ser. No. 09/553,662, filed Apr. 21, 2000; which is a continuation-in-part of Ser. No. 09/337,827, filed Jun. 22, 1999; which is a divisional of Ser. No. 08/953,326, filed Oct. 17, 1997, now U.S. Pat. No. 6,251,872; which is a continuation-in-part of application Ser. No. 08/733,230, filed Oct. 17, 1996, now U.S. Pat. No. 6,025,338. This application also claims priority to provisional application Serial No. 60/130,725, filed Apr. 22, 1999, and provisional application Serial No. 60/269,944, filed Feb. 20, 2001. Each of these patent applications is herein incorporated by referenec in its entirety, including all figures, nucleic acid sequences, amino acid sequences, drawings, and tables.

This invention was made with government support under USAID Grant No. LAG-1328-G-00-3030-00. The government has certain rights in this invention.

TECHNICAL FIELD

This invention relates to nucleic acid vaccines for rickettsial diseases of animals, including humans.

BACKGROUND OF THE INVENTION

The rickettsias are a group of small bacteria commonly transmitted by arthropod vectors to man and animals, in which they may cause serious disease. The pathogens causing human rickeltsial diseases include the agent of epidemic typhus, *Rickettsia prowazekii,* which has resulted in the deaths of millions of people during wartime and natural disasters. The causative agents of spotted fever, e.g., *Rickettsia rickettsii* and *Rickettsia conorii,* are also included within this group. Recently, new types of human rickettsial disease caused by members of the tribe Ehrlichiae have been described. Ehrlichiae infect leukocytes and endothelial cells of many different mammalian species, some of them causing serious human and veterinary diseases. Over 400 cases of human ehrlichiosis, including some fatalities, caused by *Ehrlichia chaffeensis* have now been reported. Clinical signs of human ehrlichiosis are similar to those of Rocky Mountain spotted fever, including fever, nausea, vomiting, headache, and rash.

Heartwater is another infectious disease caused by a rickettsial pathogen, namely *Cowdria ruminantium,* and is transmitted by ticks of the genus Amblyomma. The disease occurs throughout most of Africa and has an estimated endemic area of about 5 million square miles. In endemic areas, heartwater is a latent infection in indigenous breeds of cattle that have been subjected to centuries of natural selection. The problems occur where the disease contacts susceptible or naive cattle and other ruminants. Heartwater has been confirmed to be on the island of Guadeloupe in the Caribbean and is spreading through the Caribbean Islands. The tick vectors responsible for spreading this disease are already present on the American mainland and threaten the livestock industry in North and South America.

In acute cases of heartwater, animals exhibit a sudden rise in temperature, signs of anorexia, cessation of rumination, and nervous symptoms including staggering, muscle twitching, and convulsions. Death usually occurs during these convulsions. Peracute cases of the disease occur where the animal collapses and dies in convulsions having shown no preliminary symptoms. Mortality is high in susceptible animals. Angora sheep infected with the disease have a 90% mortality rate while susceptible cattle strains have up to a 60% mortality rate.

If detected early, tetracycline or chloramphenicol treatment are effective against rickettsial infections, but symptoms are similar to numerous other infections and there are no satisfactory diagnostic tests (Helmick, C., K. Bernard, L. D'Angelo [1984] *J. Infect. Dis.* 150:480).

Animals which have recovered from heartwater are resistant to further homologous, and in some cases heterologous, strain challenge. It has similarly been found that persons recovering from a rickettsial infection may develop a solid and lasting immunity. Individuals recovered from natural infections are often immune to multiple isolates and even species. For example, guinea pigs immunized with a recombinant *R. conorii* protein were partially protected even against *R. rickettsii* (Vishwanath, S., G. McDonald, N. Watkins [1990] *Infect. Immun.* 58:646). It is known that there is structural variation in rickettsial antigens between different geographical isolates. Thus, a functional recombinant vaccine against multiple isolates would need to contain multiple epitopes, e.g., protective T and B cell epitopes, shared between isolates. It is believed that serum antibodies do not play a significant role in the mechanism of immunity against rickettsia (Uilenberg, G. [1983]*Advances in Vet. Sci. and Comp. Med.* 27:427–480; Du Plessis, Plessis, J. L. [1970] *Onderstepoort J. Vet. Res.* 37(3):147–150).

Vaccines based on inactivated or attenuated rickettsiae have been developed against certain rickettsial diseases, for example against *R. prowazekii* and *R. rickettsii.* However, these vaccines have major problems or disadvantages, including undesirable toxic reactions, difficulty in standardization, and expense (Woodward, T. [1981] "Rickettsial diseases: certain unsettled problems in their historical perspective," In *Rickettsia and Rickettsial Diseases,* W. Burgdorfer and R. Anacker, eds., Academic Press, New York, pp. 17–40).

A vaccine currently used in the control of heartwater is composed of live infected sheep blood. This vaccine also has several disadvantages. First, expertise is required for the intravenous inoculation techniques required to administer this vaccine. Second, vaccinated animals may experience shock and so require daily monitoring for a period after vaccination. There is a possibility of death due to shock throughout this monitoring period, and the drugs needed to treat any shock induced by vaccination are costly. Third, blood-borne parasites may be present in the blood vaccine and be transmitted to the vaccinates. Finally, the blood vaccine requires a cold chain to preserve the vaccine.

Clearly, a safer, more effective vaccine that is easily administered would be particularly advantageous. For these reasons, and with the advent of new methods in biotechnology, investigators have concentrated recently on the development of new types of vaccines, including recombinant vaccines. However, recombinant vaccine antigens must be carefully selected and presented to the immune system such that shared epitopes are recognized. These factors have contributed to the search for effective vaccines.

A protective vaccine against rickettsiae that elicits a complete immune response can be advantageous. A few antigens which potentially can be useful as vaccines have now been identified and sequenced for various pathogenic rickettsia. The genes encoding the antigens and that can be employed to recombinantly produce those antigen have also been identified and sequenced. Certain protective antigens identified for *R. rickettsii, R. conorii,* and *R. prowazekii* (e.g., rOmpA and rOmpB) are large (>100 kDa), dependent on retention of native conformation for protective efficacy, but are often degraded when produced in recombinant systems. This presents technical and quality-control problems if purified recombinant proteins are to be included in a vaccine. The mode of presentation of a recombinant antigen to the immune system can also be an important factor in the immune response.

Nucleic acid vaccination has been shown to induce protective immune responses in non-viral systems and in diverse animal species (Special Conference Issue, WHO meeting on nucleic acid vaccines [1994] *Vaccine* 12:1491). Nucleic acid vaccination has induced cytotoxic lymphocyte (CTL), T-helper 1, and antibody responses, and has been shown to be protective against disease (Ulmer, J., J. Donelly, S. Parker et al. [1993] *Science* 259:1745). For example, direct intramuscular injection of mice with DNA encoding the influenza nucleoprotein caused the production of high titer antibodies, nucleoprotein-specific CTLs, and protection against viral challenge. Immunization of mice with plasmid DNA encoding the *Plasmodium yoelii* circumsporozoite protein induced high antibody titers against malaria sporozoites and CTLs, and protection against challenge infection (Sedegah, M., R. Hedstrom, P. Hobart, S. Hoffman [1994] *Proc. Natl. Acad. Sci. USA* 91:9866). Cattle immunized with plasmids encoding bovine herpesvirus 1 (BHV-1) glycoprotein IV developed neutralizing antibody and were partially protected (Cox, G., T. Zamb, L. Babiuk [1993] *J. Virol.* 67:5664). However, it has been a question in the field of immunization whether the recently discovered technology of nucleic acid vaccines can provide improved protection against an antigenic drift variant. Moreover, it has not heretofore been recognized or suggested that nucleic acid vaccines may be successful to protect against rickettsial disease or that a major surface protein conserved in rickettsia was protective against disease.

BRIEF SUMMARY OF THE INVENTION

Disclosed and claimed here are novel vaccines for conferring immunity to rickettsia infection, including *Cowdria ruminantium* causing heartwater. Also disclosed are novel nucleic acid compositions and methods of using those compositions, including to confer immunity in a susceptible host. Also disclosed are novel materials and methods for diagnosing infections by Ehrlichia in humans or animals.

One aspect of the subject invention concerns a nucleic acid, e.g., DNA or mRNA, vaccine containing the major antigenic protein 1 gene (MAP1) or the major antigenic protein 2 gene (MAP2) of rickettsial pathogens. In one embodiment, the nucleic acid vaccines can be driven by the human cytomegalovirus (HCMV) enhancer-promoter. In studies immunizing mice by intramuscular injection of a DNA vaccine composition according to the subject invention, immunized mice seroconverted and reacted with MAP1 in antigen blots. Splenocytes from immunized mice, but not from control mice immunized with vector only, proliferated in response to recombinant MAP1 and rickettsial antigens in in vitro lymphocyte proliferation tests. In experiments testing different DNA vaccine dose regimens, increased survival rates as compared to controls were observed on challenge with rickettsia. Accordingly, the subject invention concerns the discovery that DNA vaccines can induce protective immunity against rickettsial disease or death resulting therefrom.

The subject invention further concerns the genes designated *Cowdria ruminantium* map 2, *Cowdria ruminantium* 1hworf3, *Cowdria ruminantium* 4hworf1, *Cowdria ruminantium* 18hworf1, and *Cowdria ruminantium* 3*gdorf*3 and the use of these genes in diagnostic and therapeutic applications. The subject invention further concerns the proteins encoded by the exemplified genes, antibodies to these proteins, and the use of such antibodies and proteins in diagnostic and therapeutic applications.

In one embodiment of the subject invention, the polynucleotide vaccines are administered in conjunction with an antigen. In a preferred embodiment, the antigen is the polypeptide which is encoded by the polynucleotide administered as the polynucleotide vaccine. As a particularly preferred embodiment, the antigen is administered as a booster subsequent to the initial administration of the polynucleotide vaccine.

BRIEF DESCRIPTION OF THE DRAWINGS

FIGS. 1A–1C show a comparison of the amino acid sequences from alignment of the three rickettsial proteins, namely, *Cowdria ruminantium* (C.r.), *Ehrlichia chaffeensis* (E.c.), and *Anaplasma marginale (A.m.).*

FIGS. 2A–2C shows the DNA sequence of the 28 kDa gene locus cloned from *E. chaffeensis* (FIG. 2A–2B) and *E. canis* (FIG. 2C). One letter amino acid codes for the deduced protein sequences are presented below the nucleotide sequence. The proposed sigma-70-like promoter sequences (38) are presented in bold and underlined text as −10 and −35 (consensus −35 and −10 sequences are TTGACA and TATAAT, respectively). Similarly, consensus ribosomal binding sites and transcription terminator sequences (bold letter sequence) are identified. G-rich regions identified in the *E. chaffeensis* sequence are underlined. The conserved sequences from within the coding regions selected for RT-PCR assay are identified with italics and underlined text.

FIG. 3A shows the complete sequence of the MAP2 homolog of *Ehrlichia canis.* The arrow (→) represents the predicted start of the mature protein. The asterisk (*) represents the stop codon. Underlined nucleotides 5' to the open reading frame with −35 and −10 below represent predicted promoter sequences. Double underlined nucleotides represent the predicted ribosomal binding site. Underlined nucleotides 3' to the open reading frame represent possible transcription termination sequences.

FIG. 3B shows the complete sequence of the MAP2 homolog of *Ehrlichia chaffeensis.* The arrow (→) represents the predicted start of the mature protein. The asterisk (*) represents the stop codon. Underlined nucleotides 5' to the open reading frame with −35 and −10 below represent predicted promoter sequences. Double underlined nucleotides represent the predicted ribosomal binding site. Underlined nucleotides 3' to the open reading frame represent possible transcription termination sequences.

BRIEF DESCRIPTION OF THE SEQUENCES

SEQ ID NO. 1 is the coding sequence of the MAP1 gene from *Cowdria ruminantium* (Highway isolate).

SEQ ID NO. 2 is the polypeptide encoded by the polynucleotide of SEQ ID NO. 1.

SEQ ID NO. 3 is the coding sequence of the MAP1 gene from *Ehrlichia chaffeensis.*

SEQ ID NO. 4 is the polypeptide encoded by the polynucleotide of SEQ ID NO. 3.

SEQ ID NO. 5 is the *Anaplasma marginale* MSP4 gene coding sequence.

SEQ ID NO. 6 is the polypeptide encoded by the polynucleotide of SEQ ID NO. 5.

SEQ ID NO. 7 is a partial coding sequence of the VSA1 gene from *Ehrlichia chaffeensis,* also shown in FIGS. 2A–2B.

SEQ ID NO. 8 is the coding sequence of the VSA2 gene from *Ehrlichia chaffeensis,* also shown in FIGS. 2A–2B.

SEQ ID NO. 9 is the coding sequence of the VSA3 gene from *Ehrlichia chaffeensis,* also shown in FIGS. 2A–2B.

SEQ ID NO. 10 is the coding sequence of the VSA4 gene from *Ehrlichia chaffeensis,* also shown in FIGS. 2A–2B.

SEQ ID NO. 11 is a partial coding sequence of the VSA5 gene from *Ehrlichia chaffeensis,* also shown in FIGS. 2A–2B.

SEQ ID NO. 12 is the coding sequence of the VSA1 gene from *Ehrlichia canis,* also shown in FIG. 2C.

SEQ ID NO. 13 is a partial coding sequence of the VSA2 gene from *Ehrlichia canis,* also shown in FIG. 2C.

SEQ ID NO. 14 is the polypeptide encoded by the polynucleotide of SEQ ID NO. 7, also shown in FIGS. 2A–2B.

SEQ ID NO. 15 is the polypeptide encoded by the polynucleotide of SEQ ID NO. 8, also shown in FIGS. 2A–2B.

SEQ ID NO. 16 is the polypeptide encoded by the polynucleotide of SEQ ID NO. 9, also shown in FIGS. 2A–2B.

SEQ ID NO. 17 is the polypeptide encoded by the polynucleotide of SEQ ID NO. 10, also shown in FIGS. 2A–2B.

SEQ ID NO. 18 is the polypeptide encoded by the polynucleotide of SEQ ID NO. 11, also shown in FIGS. 2A–2B.

SEQ ID NO. 19 is the polypeptide encoded by the polynucleotide of SEQ ID NO. 12, also shown in FIG. 2C.

SEQ ID NO. 20 is the polypeptide encoded by the polynucleotide of SEQ ID NO. 13, also shown in FIG. 2C.

SEQ ID NO. 21 is the coding sequence of the MAP2 gene from *Ehrlichia canis,* also shown in FIG. 3A.

SEQ ID NO. 22 is the coding sequence of the MAP2 gene from *Ehrlichia chaffeensis,* also shown in FIG. 3B.

SEQ ID NO. 23 is the polypeptide encoded by the polynucleotide of SEQ ID NO. 21, also shown in FIG. 3A.

SEQ ID NO. 24 is the polypeptide encoded by the polynucleotide of SEQ ID NO. 22, also shown in FIG. 3B.

SEQ ID NO. 25 is the coding sequence of the map2 gene from *Cowdria ruminantium.*

SEQ ID NO. 26 is the polypeptide encoded by the polynucleotide of SEQ ID NO. 25.

SEQ ID NO. 27 is the coding sequence of the 4hworf3 gene from *Cowdria ruminantium.*

SEQ ID NO. 28 is the polypeptide encoded by the polynucleotide of SEQ ID NO. 27.

SEQ ID NO. 29 is the coding sequence of the 4hworf1 gene from *Cowdria ruminantium.*

SEQ ID NO. 30 is the polypeptide encoded by the polynucleotide of SEQ ID NO. 29.

SEQ ID NO. 31 is the coding sequence of the 18hworf1 gene from *Cowdria ruminantium.*

SEQ ID NO. 32 is the polypeptide encoded by the polynucleotide of SEQ ID NO. 31.

SEQ ID NO. 33 is the coding sequence of the 3gdorf3 gene from *Cowdria ruminantium.*

SEQ ID NO. 34 is the polypeptide encoded by the polynucleotide of SEQ ID NO. 33.

DETAILED DISCLOSURE OF THE INVENTION

In one embodiment, the subject invention concerns a novel strategy, termed nucleic acid vaccination, for eliciting an immune response protective against rickettsial disease. The subject invention also concerns novel compositions that can be employed according to this novel strategy for eliciting a protective immune response.

According to the subject invention, recombinant DNA or mRNA encoding an antigen of interest is inoculated directly into the human or animal host where an immune response is induced. Prokaryotic signal sequences may be deleted from the nucleic acid encoding an antigen of interest. Advantageously, problems of protein purification, as can be encountered with antigen delivery using live vectors, can be virtually eliminated by employing the compositions or methods according to the subject invention. Unlike live vector delivery, the subject invention can provide a further advantage in that the DNA or RNA does not replicate in the host, but remains episomal. See, for example, Wolff, J. A., J. J. Ludike, G. Acsadi, P. Williams, A,. Jani (1992) *Hum. Mol. Genet.* 1:363. A complete immune response can be obtained as recombinant antigen is synthesized intracellularly and presented to the host immune system in the context of autologous class I and class II MHC molecules.

In one embodiment, the subject invention concerns nucleic acids and compositions comprising those nucleic acids that can be effective in protecting an animal from disease or death caused by rickettsia. For example, a nucleic acid vaccine of the subject invention has been shown to be protective against *Cowdria ruminantium,* the causative agent of heartwater in domestic ruminants. Accordingly, nucleotide sequences of rickettsial genes, as described herein, can be used as nucleic acid vaccines against human and animal rickettsial diseases.

In one embodiment of the subject invention, the polynucleotide vaccines are administered in conjunction with an antigen. In a preferred embodiment, the antigen is the polypeptide which is encoded by the polynucleotide administered as the polynucleotide vaccine. As a particularly preferred embodiment, the antigen is administered as a booster subsequent to the initial administration of the polynucleotide vaccine. In another embodiment of the invention, the polynucleotide vaccine is administered in the form of a "cocktail" which contains at least two of the nucleic acid vaccines of the subject invention. The "cocktail" may be administered in conjunction with an antigen or an antigen booster as described above.

The MAP1 gene, which can be used to obtain this protection, is also present in other rickettsiae including *Anaplasma marginale, Ehrlichia canis,* and in a causative agent of human ehrlichiosis, *Ehrlichia chaffeensis* (van Vliet, A., F. Jongejan, M. van Kleef, B. van der Zeijst [1994] *Infect. Immun.* 62:1451). The MAP1 gene or a MAP1-like gene can also be found in certain Rickettsia spp. MAP1-like genes from *Ehrlichia chaffeensis* and *Ehrlichia canis* have now been cloned and sequenced. These MAP-1 homologs are also referred to herein as Variable Surface Antigen (VSA) genes.

The present invention also concerns polynucleotides encoding MAP2 or MAP2 homologs from *Ehrlichia canis* and *Ehrlichia chaffeensis.* MAP2 polynucleotide sequences of the invention can be used as vaccine compositions and in diagnostic assays. The polynucleotides can also be used to produce the MAP2 polypeptides encoded thereby.

The subject invention further concerns the genes designated *Cowdria ruminantium* map 2, *Cowdria ruminantium*

1*hworf*3, *Cowdria ruminantium* 4hworf1, *Cowdria ruminantium* 18*hworf*1, and *Cowdria ruminantium* 3*gdorf*3 and the use of these genes in diagnostic and therapeutic applications. The subject invention further concerns the proteins encoded by the exemplified genes, antibodies to these proteins, and the use of such antibodies and proteins in diagnostic and therapeutic applications.

Compositions comprising the subject polynucleotides can include appropriate nucleic acid vaccine vectors (plasmids), which are commercially available (e.g., Vical, San Diego, Calif.). In addition, the compositions can include a pharmaceutically acceptable carrier, e.g., saline. The pharmaceutically acceptable carriers are well known in the art and also are commercially available. For example, such acceptable carriers are described in E. W. Martin's *Remington's Pharmaceutical Science,* Mack Publishing Company, Easton, Pa.

The subject invention also concerns polypeptides encoded by the subject polynucleoticles. Specifically exemplified are the polypeptides encoded by the MAP-1 and VSA genes of *C. rumimontium, E. chaffeensis, E. canis* and the MP4 gene of *Anaplasma marginale.* Polypeptides uncoded by *E. chaffeensis* and *E. canis* MAP2 genes are also exemplified herein.

Also encompassed within the scope of the present invention are fragments and variants of the exemplified polynucleotides and polypeptides. Fragments would include, for example, portions of the exemplified sequences wherein procaryotic signal sequences have been removed. Examples of the removal of such sequences are given in Example 3. Variants include polynucleotides and/or polypeptides having base or amino acid additions, deletions and substitutions in the sequence of the subject molecule so long as those variants have substantially the same activity or serologic reactivity as the native molecules. Also included are allelic variants of the subject polynucleotides. The polypeptides of the present invention can be used to raise antibodies that are reactive with the polypeptides disclosed herein. The polypeptides and polynucleotides can also be used as molecular weight markers.

Another aspect of the subject invention concerns antibodies reactive with MAP-1 and MAP2 polypeptides disclosed herein. Antibodies can be monoclonal or polyclonal and can be produced using standard techniques known in the art. Antibodies of the invention can be used in diagnostic and therapeutic applications.

In a specific embodiment, the subject invention concerns a DNA vaccine (e.g., VCL1010/MAP1) containing the major antigenic protein 1 gene (MAP1) driven by the human cytomegalovirus (HCMV) enhancer-promoter. In a specific example, this vaccine was injected intramuscularly into 8–10 week-old female DBA/2 mice after treating them with 50 $\mu$l/muscle of 0.5% bupivacaine 3 days previously. Up to 75% of the VCL1010/MAP1-immunized mice seroconverted and reacted with MAP1 in antigen blots. Splenocytes from immunized mice, but not from control mice immunized with VCL1010 DNA (plasmid vector, Vical, San Diego) proliferated in response to recombinant MAP1 and *C. ruminantium* antigens in in vitro lymphocyte proliferation tests. These proliferating cells from mice immunized with VCL1010/MAP1 DNA secreted IFN-gamma and IL-2 at concentrations ranging from 610 pg/ml and 152 pg/ml to 1290 pg/ml and 310 pg/ml, respectively. In experiments testing different VCL1010/MAP1 DNA vaccine dose regimens (25–100 $\mu$g/dose, 2 or 4 immunizations), survival rates of 23% to 88% (35/92 survivors/total in all VCL1010/MAP1 immunized groups) were observed on challenge with 30LD50 of *C. ruminantium.* Survival rates of 0% to 3% (1/144 survivors/total in all control groups) were recorded for control mice immunized similarly with VCL1010 DNA or saline. Accordingly, in a specific embodiment, the subject invention concerns the discovery that the gene encoding the MAP1 protein induces protective immunity as a DNA vaccine against rickettsial disease.

The nucleic acid sequences described herein have other uses as well. For example, the nucleic acids of the subject invention can be useful as probes to identify complementary sequences within other nucleic acid molecules or genomes. Such use of probes can be applied to identify or distinguish infectious strains of organisms in diagnostic procedures or in rickettsial research where identification of particular organisms or strains is needed. As is well known in the art, probes can be made by labeling the nucleic acid sequences of interest according to accepted nucleic acid labeling procedures and techniques. A person of ordinary skill in the art would recognize that variations or fragments of the disclosed sequences which can specifically and selectively hybridize to the DNA of rickettsia can also function as a probe. It is within the ordinary skill of persons in the art, and does not require undue experimentation in view of the description provided herein, to determine whether a segment of the claimed DNA sequences is a fragment or variant which has characteristics of the full sequence, e.g., whether it specifically and selectively hybridizes or can confer protection against rickettsial infection in accordance with the subject invention. In addition, with the benefit of the subject disclosure describing the specific sequences, it is within the ordinary skill of those persons in the art to label hybridizing sequences to produce a probe.

Various degrees of stringency of hybridization can be employed. The more severe the conditions, the greater the complementarity that is required for duplex formation. Severity of conditions can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes,* Stockton Press, New York, N.Y., pp. 169–170.

Examples of various stringency conditions are provided herein. Hybridization of immobilized DNA on Southern blots with 32P-labeled gene-specific probes can be performed by standard methods (Maniatis et al. (1982) *Molecular Cloning: A Laboratory Manual,* Cold Spring Harbor Laboratory, New York.). In general, hybridization and subsequent washes can be carried out under moderate to high stringency conditions that allow for detection of target sequences with homology to the exemplified polynucleotide sequence. For double-stranded DNA gene probes, hybridization can be carried out overnight at 20-25° C. below the melting temperature (Tm) of the DNA hybrid in 6×SSPE, 5×Denhardt's solution, 0.1% SDS, 0.1 mg/ml denatured DNA. The melting temperature is described by the following formula (Beltz et al. et al. [1983] *Methods of Enzymology,* R. Wu, L. Grossman and K. Moldave [eds.] Academic Press, New York 100:266–285).

Tm=81.5° C.+16.6 Log [Na+]+0.41(% G+C)-0.61(% formamide)-600/length of duplex in base pairs.

Washes are typically carried out as follows:

(1) twice at room temperature for 15 minutes in 1×SSPE, 0.1% SDS (low stringency wash);

(2) once at Tm−20° C. for 15 minutes in 0.2×SSPE, 0.1% SDS (moderate stringency wash).

For oligonucleotide probes, hybridization can be carried out overnight at 10–20° C. below the melting temperature (Tm) of the hybrid in 6×SSPE, 5×Denhardt's solution, 0.1% SDS, 0.1 mg/ml denatured DNA. Tm for oligonucleotide probes can be determined by the following formula:

Tm (° C.)=2(number T/A base pairs)+4(number G/C base pairs) (Suggs et al. [1981] *ICN-UCLA Symp. Dev. Biol. Using Purified Genes,* D. D. Brown [ed.], Academic Press, New York, 23:683–693).

Washes can be carried out as follows:

(1) twice at room temperature for 15 minutes 1×SSPE, 0.1% SDS (low stringency wash;

(2) once at the hybridization temperature for 15 minutes in 1×SSPE, 0.1% SDS (moderate stringency wash).

In general, salt and/or temperature can be altered to change stringency. With a labeled DNA fragment >70 or so bases in length, the following conditions can be used:

| | |
|---|---|
| Low: | 1 or 2X SSPE, room temperature |
| Low: | 1 or 2X SSPE, 42° C. |
| Moderate: | 0.2X or 1X SSPE, 65° C. |
| High: | 0.1X SSPE, 65° C. |

Duplex formation and stability depend on substantial complementarity between the two strands of a hybrid and, as noted above, a certain degree of mismatch can be tolerated. Therefore, the probe sequences of the subject invention include mutations (both single and multiple), deletions, insertions of the described sequences, and combinations thereof, wherein said mutations, insertions and deletions permit formation of stable hybrids with the target polynucleotide of interest. Mutations, insertions and deletions can be produced in a given polynucleotide sequence in many ways, and these methods are known to an ordinarily skilled artisan. Other methods may become known in the future.

It is also well known in the art that restriction enzymes can be used to obtain functional fragments of the subject DNA sequences. For example, Bal31 exonuclease can be conveniently used for time-controlled limited digestion of DNA (commonly referred to as "erase-a-base" procedures). See, for example, Maniatis et al (1982) *Molecular Cloning: A Laboratory Manual,* Cold Spring Harbor Laboratory, New York; Wei et al. (1983) *J. Biol. Chem.* 258:13006–13512.

In addition, the nucleic acid sequences of the subject invention can be used as molecular weight markers in nucleic acid analysis procedures.

Following are examples which illustrate procedures for practicing the invention. These examples should not be construed as limiting. All percentages are by weight and all solvent mixture proportions are by volume unless otherwise noted.

EXAMPLE 1

A nucleic acid vaccine construct was tested in animals for its ability to protect against death caused by infection with the rickettsia *Cowdria ruminantium.* The vaccine construct tested was the MAP1 gene of *C. ruminantium* inserted into plasmid VCL1010 (Vical, San Diego) under control of the human cytomegalovirus promoter-enhancer and intron A. In this study, seven groups containing 10 mice each were injected twice at 2-week intervals with either 100, 75, 50, or 25 μg VCL1010/MAP1 DNA (V/M in Table 1 below), or 100, 50 μg VCL1010 DNA (V in Table 1) or saline (Sal.), respectively. Two weeks after the last injections, 8 mice/group were challenged with 30LD50 of *C. ruminantium* and clinical symptoms and survival monitored. The remaining 2 mice/group were not challenged and were used for lymphocyte proliferation tests and cytokine measurements. The results of the study are summarized in Table 1, below:

TABLE 1

| | 100 μg V/M | 75 μg V/M | 50 μg V/M | 25 μg V/M | 100 μg V | 50 μg V | Sal. |
|---|---|---|---|---|---|---|---|
| Survived | 5 | 7 | 5 | 3 | 0 | 0 | 0 |
| Died | 3 | 1 | 3 | 5 | 8 | 8 | 8 |

The VCL1010/MAP1 nucleic acid vaccine increased survival on challenge in all groups, with a total of 20/30 mice surviving compared to 0/24 in the control groups.

This study was repeated with another 6 groups, each containing 33 mice (a total of 198 mice). Three groups received 75 μg VCL1010/MAP1 DNA or VCL1010 DNA or saline (4 injections in all cases). Two weeks after the last injection, 30 mice/group were challenged with 30LD50 of *C. ruminantium* and 3 mice/group were sacrificed for lymphocyte proliferation tests and cytokine measurements. The results of this study are summarized in Table 2, below:

TABLE 2

| | V/M 2 inj. | V 2 inj. | Sal. 2 inj. | V/M 4 inj. | V 4 inj. | Sal. 4 inj. |
|---|---|---|---|---|---|---|
| Survived | 7 | 0 | 0 | 8 | 0 | 1 |
| Died* | 23 | 30 | 30 | 22 | 30 | 29 |

*In mice that died in both V/M groups, there was an increase in mean survival time of approximately 4 days compared to the controls ($p < 0.05$).

Again, as summarized in Table 2, the VCL1010/MAP1 DNA vaccine increased the numbers of mice surviving in both immunized groups, although there was no apparent benefit of 2 additional injections. In these two experiments, there were a cumulative total of 35/92 (38%) surviving mice in groups receiving the VCL1010/MAP1 DNA vaccine compared to 1/144(0.7%) surviving mice in the control groups. In both immunization and challenge trials described above, splenocytes from VCL1010/MAP1 immunized mice, but not from control mice, specifically proliferated to recombinant MAP1 protein and to *C. ruminantium* in lymphocyte proliferation tests. These proliferating splenocytes secreted IL-2 and gamma-interferon at concentrations up to 310 and 1290 pg/ml respectively. These data show that protection against rickettsial infections can be achieved with a DNA vaccine. In addition, these experiments show MAP1-related proteins as vaccine targets.

EXAMPLE 2

Cloning and Sequence Analysis of MAP1 Homologue Genes of *E. chaffeensis* and *E. canis*

Genes homologous to the major surface protein of *C. ruminantium* MAP1 were cloned from *E. chaffeensis* and *E. canis* by using PCR cloning strategies. The cloned segments represent a 4.6 kb genomic locus of *E. chaffeensis* and a 1.6 kb locus of *E. canis.* DNA sequence generated from these clones was assembled and is presented along with the deduced amino acid sequence in FIGS. 2A–2B (SEQ ID NOs. 7–11 and 14–18) and FIG. 2C (SEQ ID NOs. 12–13 and 19–20). Significant features of the DNA include five very similar but nonidentical open reading frames (ORFs) for *E. chaffeensis* and two very similar, nonidentical ORFs for the *E. canis* cloned locus. The ORFs for both Ehrlichia spp. are separated by noncoding sequences ranging from 264 to 310 base pairs. The noncoding sequences have a higher A+T content (71.6% for *E. chaffeensis* and 76.1% for *E. canis*) than do the coding sequences (63.5% for *E. chaffeensis* and 68.0% for *E. canis*). A G-rich region −200 bases upstream from the initiation codon, sigma-70-like promoter sequences, putative ribosome binding sites (RBS), termination codons, and palindromic sequences near the termination codons are found in each of the *E. chaffeensis* noncoding sequences. The *E. canis* noncoding sequence has the same feature except for the G-rich region (FIG. 2C; SEQ ID NOs. 12–13 and 19–20).

Sequence comparisons of the ORFs at the nucleotide and translated amino acid levels revealed a high degree of similarity between them. The similarity spanned the entire coding sequences, except in three regions where notable sequence variations were observed including some deletions/insertions (Variable Regions I, II and III). Despite the similarities, no two ORFs are identical. The cloned ORF 2, 3 and 4 of *E. chaffeensis* have complete coding sequences. The ORF1 is a partial gene having only 143 amino acids at the C-terminus whereas the ORF5 is nearly complete but lacks 5–7 amino acids and a termination codon. The cloned ORF2 of *E. canis* also is a partial gene lacking a part of the C-terminal sequence. The overall similarity between different ORFs at the amino acid level is 56.0% to 85.4% for *E. chaffeensis,* whereas for *E. canis* it is 53.3%. The similarity of *E. chaffeensis* ORFs to the MAP1 coding sequences reported for *C. ruminantium* isolates ranged from 55.5% to 66.7%, while for *E. canis* to *C. ruminantium* it is 48.5% to 54.2%. Due to their high degree of similarity to MAP1 surface antigen genes of *C. ruminantium* and since they are nonidentical to each other, the *E. chaffeensis* and *E. canis* ORFs are referred to herein as putative Variable Surface Antigen (VSA) genes. The apparent molecular masses of the predicted mature proteins of *E. chaffeensis* were 28.75 kDa for VSA2, 27.78 for VSA3, and 27.95 for VSA4, while *E. canis* VSA1 was slightly higher at 29.03 kDa. The first 25 amino acids in each VSA coding sequence were eliminated when calculating the protein size since they markedly resembled the signal sequence of *C. ruminantium* MAP1 and presumably would be absent from the mature protein.

The amino acid sequence derived from the cloned *E. chaffeensis* MAP1-like gene, and alignment with the corresponding genes of *C. ruminantium* and *A. marginale* is shown in FIG. 1.

EXAMPLE 3

A further aspect of the subject invention are five additional genes which give protection when formatted as DNA vaccines. These genes are *Cowdria ruminantium* map 2, *Cowdria ruminantium* 1*hworf*3, *Cowdria ruminantium* 4*hworf*1, *Cowdria ruminantium* 18*hworf*1, and *Cowdria ruminantium* 3*gdorf*3. The DNA and translated amino acid sequences of these five genes are shown in SEQ ID NOS. 25–34.

There is published information showing that gene homologs of all five genes are present in other bacteria. For example, a homolog of map2 is present in *Anaplasma marginale,* a homolog of 1hworf3 is present in *Brucella abortus,* homologs of 4hworf1 are present in *Pseudomonas aeruginosa* and *Coxiella burnetii,* and homologs of 18hworf1 are present in *Coxiella burnetii* and *Rickettsia prowazekii.* This can be revealed by a search of DNA and protein databases with standard search algorithms such as "Blast". Based on the protective ability of these genes against *Cowdria ruminantium* and their presence in other bacterial pathogens, the subject invention further concerns the use of these genes, their gene products, and the genes and gene products of the homologs as vaccines against bacteria. This includes their use as DNA or nucleic acid vaccines or when formulated in vaccines employing other methods of delivery, e.g., recombinant proteins or synthetic peptides in adjuvants, recombinant live vector delivery systems such as vaccinia (or other live viruses) or Salmonella (or other live bacteria). These methods of delivery are standard to those familiar with the field. This also includes vaccines against heartwater disease, vaccines against rickettsial diseases in general and vaccines against other bacteria containing homologs of these genes.

Table 3 shows the protective ability of the 5 genes against death from *Cowdria ruminantium* challenge in mice. Genes were inserted into VR1012 according to the manufacturers instructions (Vical, San Diego) and challenge studies were conducted as described in Example 1. N-terminal sequences which putatively encoded prokaryotic signal peptides were deleted because of the potential for their affects on expression and and immune responses in eukaryotic expression systems or challenged animals. The inserts were as follows: map2, SEQ ID NO. 25, beginning at base 46; 18hworf1, SEQ ID NO.31, beginning at base 67; 3gdorf3, SEQ ID NO. 33, beginning at base 79; 1hworf3, SEQ ID NO. 27, beginning at base 76; and 4hworf1, SEQ ID NO. 29, beginning at base 58.

TABLE 3

| | MWT | Survival Rate | | | | |
|---|---|---|---|---|---|---|
| DNA Construct | Size | Vaccinated | | Control | | P value |
| TMMAP2 | 21 kd | 9/28* | 32% | 0/29 | 0% | 0.004 |
| MB18HWORF1 | 28 kd | 10/30* | 33% | 1/27 | 4% | 0.021 |
| AM3GDORF3 | 16 kd | 7/26 | 27% | 1/27 | 4% | 0.060 |
| TM1HWORF3 | 36 kd | 8/29 | 28% | 2/30 | 7% | 0.093 |
| TM4HWORF1 | 19 kd | 10/30* | 33% | 2/30 | 7% | 0.054 |

Control - VR1012 DNA vector plasmid only
*Statistically significant difference (Fisher's Exact test)

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. An isolated polynucleotide which encodes: a) the polypeptide set forth in SEQ ID NO:32; or b) immunogenic fragments of the polypeptide set forth in SEQ ID NO:32.

2. The isolated polynucleotide of claim 1, wherein the polynucleotide encodes the polypeptide set forth in SEQ ID NO:32 and comprises the nucleic acid sequence as set forth in SEQ ID NO:31.

3. The isolated polynucleotide of claim 1, wherein the isolated polynucleotide encodes an immunogenic fragment of the polypeptide set forth in SEQ ID NO:32 and comprises a polynucleotide sequence that begins at nucleotide base 67 as set forth in SEQ ID NO:31.

4. A vector comprising an isolated polynucleotide selected from the group of:

a) an isolated polynucleotide which encodes the polypeptide set forth in SEQ ID NO:32;

b) an isolated polynucleotide that encodes immunogenic fragments of the polypeptide set forth in SEQ ID NO:32;

c) an isolated polynucleotide which comprises the nucleic acid sequence as set forth in SEQ ID NO:31; and d) an isolated polynucleotide which encodes an immunogenic fragment of the polypeptide set forth in SEQ ID NO:32 and comprises a polynucleotide sequence that begins at nucleotide base 67 as set forth in SEQ ID NO:31.

5. An isolated polynucleotide which encodes the polypeptide set forth in SEQ ID NO:32 or fragments thereof, wherein said polypeptide or fragments thereof have the characteristic of eliciting an immune response protective against disease caused by Cowdria ruminatium.

6. The isolated polynucleotide of claim 5, further comprising a nucleic acid vector.

7. The isolated polynucleotide of claim 6, wherein the vector is a vaccine vector.

8. A composition comprising a pharmaceutically acceptable carrier and a nucleic acid vaccine vector comprising an operably linked isolated polynucleotide selected from the group of:

a) an isolated polynucleotide which enclodes the polypeptide set forth in SEQ ID NO:32;

b) an isolated polynucleotide that encodes immunogenic fragments of the polypeptide set forth in SEQ ID NO:32;

c) an isolated polynucleotide which comprises the nucleic acid sequence as set forth in SEQ ID NO:31; and d) an isolated polynucleotide which encodes an immunogenic fragment of the polypeptide set forth in SEQ ID NO:32 and comprises a polynucleotide sequence that begins at nucleotide base 67 as set forth in SEQ ID NO:31, wherein said composition has the characteristic of eliciting an immune response against disease caused by *Cowdria ruminantium.*

9. The composition of claim 8, wherein the isolated polynucleotide comprises the nucleic acid sequence as set forth in SEQ ID NO:31.

10. The composition of claim 8, wherein said isolated polynucleotide encodes the polypeptide set forth in SEQ ID NO:32.

11. The composition of claim 8, wherein said isolated polynucleotide encodes immunogenic fragments of the polypeptide set forth in SEQ ID NO:32.

12. The composition of claim 8, wherein said isolated polynucleotide encodes an immunogenic fragment of the polypeptide set forth in SEQ ID NO:32 and comprises a polynucleotide sequence that begins at nucleotide base 67 as set forth in SEQ ID NO:31.

13. A method for reducing the lethality of a *Cowdria ruminantium* infection in a host susceptible to infection by *Cowdria ruminantium* comprising administering the composition of claim 8 in an amount effective to reduce lethality.

14. The method of claim 13, wherein said composition comprises a pharmaceutically acceptable carrier and a nucleic acid vaccine vector comprising an operably linked isolated polynucleotide which encodes the polypeptide set forth in SEQ ID NO:32.

15. The method of claim 13, wherein said composition comprises a pharmaceutically acceptable carrier and a nucleic acid vaccine vector comprising an operably linked isolated polynucleotide which encodes fragments of the polypeptide set forth in SEQ ID NO:32.

16. The method of claim 13, wherein said composition comprises a pharmaceutically acceptable carrier and a nucleic acid vaccine vector comprising an operably linked isolated polynucleotide comprising the nucleic acid sequence as set forth in SEQ ID NO:31.

17. The method of claim 13, wherein said composition comprises a pharmaceutically acceptable carrier and a nucleic acid vaccine vector comprising an operably linked isolated polynucleotide that comprises a polynucleotide sequence that begins at nucleotide base 67 as set forth in SEQ ID NO:31.

18. A method of inducing an immune response in an animal susceptible to infection by the rickettsial pathogen *Cowdria ruminantium* comprising administering a composition comprising a pharmaceutically acceptable carrier and a nucleic acid vaccine vector comprising an operably linked isolated polynucleotide selected from the group of:

a) an isolated polynucleotide which encodes the polypeptide set forth in SEQ ID NO:32;

b) an isolated polynucleotide that encodes immunogenic fragments of the polypeptide set forth in SEQ ID NO:32;

c) an isolated polynucleotide which comprises the nucleic acid sequence as set forth in SEQ ID NO:31; and d) an isolated polynucleotide which encodes an immunogenic fragment of the polypeptide set forth in SEQ ID NO:32 and comprises a polynucleotide sequence that begins at nucleotide base 67 as set forth in SEQ ID NO:31, wherein said composition is administered in an amount effective to induce an immune response.

19. The method of claim 18, wherein said composition comprises a pharmaceutically acceptable carrier and a nucleic acid vaccine vector comprising an operably linked isolated polynucleotide which encodes the polypeptide set forth in SEQ ID NO:32.

20. The method of claim 18, wherein said composition comprises a pharmaceutically acceptable carrier and a nucleic acid vaccine vector comprising an operably linked isolated polynucleotide which encodes immunogenic fragments of the polypeptide set forth in SEQ ID NO:32.

21. The method of claim 18, wherein said composition comprises a pharmaceutically acceptable carrier and a nucleic acid vaccine vector comprising an operably linked isolated polynucleotide which comprises the nucleic acid sequence as set forth in SEQ ID NO:31.

22. The method of claim 18, wherein said composition comprises a pharmaceutically acceptable carrier and a nucleic acid vaccine vector comprising an operably linked isolated polynucleotide which comprises a polynucleotide sequence that begins at nucleotide base 67 as set forth in SEQ ID NO:31.

23. The method of claim 18, wherein said immune response is a protective immune response.

24. The method of claim 19, wherein said composition induces a protective immune response.

25. The method of claim 20, wherein said composition induces a protective immune response.

26. The method of claim 21, wherein said composition induces a protective immune response.

27. The method of claim 22, wherein said composition induces a protective immune response.

28. The vector of claim 4, wherein said vector is a vaccine vector.

29. The isolated polynucleotide of claim 1, wherein said isolated polynucleotide encodes immunogenic fragments of the polypeptide set forth in SEQ ID NO:32.

30. The isolated polynucleotide of claim 1, wherein said isolated polynucleotide encodes the polypeptide set forth in SEQ ID NO:32.

31. The vector of claim 4, wherein the isolated polynucleotide encodes immunogenic fragments of the polypeptide set forth in SEQ ID NO:32.

32. The vector of claim 4, wherein said isolated polynucleotide comprises the nucleic acid sequence as set forth in SEQ ID NO:31.

33. The vector of claim 4, wherein said isolated polynucleotide encodes an immunogenic fragment of the polypeptide set forth in SEQ ID NO:32 and comprises a polynucleotide sequence that begins at nucleotide base 67 as set forth in SEQ ID NO:31.

* * * * *

UNITED STATES PATENT AND TRADEMARK OFFICE

CERTIFICATE OF CORRECTION

PATENT NO. : 6,653,128 B2
DATED : November 25, 2003
INVENTOR(S) : Anthony Barbet et al.

It is certified that error appears in the above-identified patent and that said Letters Patent is hereby corrected as shown below:

<u>Column 1</u>,
Line 18, "by referenec in its entirety" should read -- by reference in its entirety --
Line 34, "human rickeltsial" should read -- human rickettsial --

<u>Column 5</u>,
Line 51, "sequence of the 4hworf3" should read -- sequence of the *ihworf3* --

<u>Column 7</u>,
Line 18, "by the subject polynucleoticles" should read -- polynucleotides --

Signed and Sealed this

Eleventh Day of May, 2004

JON W. DUDAS
*Acting Director of the United States Patent and Trademark Office*

SEQUENCE LISTING

```
<160> NUMBER OF SEQ ID NOS: 34

<210> SEQ ID NO 1
<211> LENGTH: 864
```

-continued

<212> TYPE: DNA
<213> ORGANISM: Cowdria ruminantium
<220> FEATURE:
<221> NAME/KEY: CDS
<222> LOCATION: (1)..(861)

<400> SEQUENCE: 1 atg aat tgc aag aaa att ttt atc aca agt aca cta ata tca tta gtg 48
Met Asn Cys Lys Lys Ile Phe Ile Thr Ser Thr Leu Ile Ser Leu Val
1 5 10 15 tca ttt tta cct ggt gtg tcc ttt tct gat gta ata cag gaa gac agc 96
Ser Phe Leu Pro Gly Val Ser Phe Ser Asp Val Ile Gln Glu Asp Ser
20 25 30 aac cca gca ggc agt gtt tac att agc gca aaa tac atg cca act gca 144
Asn Pro Ala Gly Ser Val Tyr Ile Ser Ala Lys Tyr Met Pro Thr Ala
35 40 45 tca cat ttt ggt aaa atg tca atc aaa gaa gat tca aaa aat act caa 192
Ser His Phe Gly Lys Met Ser Ile Lys Glu Asp Ser Lys Asn Thr Gln
50 55 60 acg gta ttt ggt cta aaa aaa gat tgg gat ggc gtt aaa aca cca tca 240
Thr Val Phe Gly Leu Lys Lys Asp Trp Asp Gly Val Lys Thr Pro Ser
65 70 75 80 gat tct agc aat act aat tct aca att ttt act gaa aaa gac tat tct 288
Asp Ser Ser Asn Thr Asn Ser Thr Ile Phe Thr Glu Lys Asp Tyr Ser
85 90 95 ttc aga tat gaa aac aat ccg ttt tta ggt ttc gct gga gca att ggg 336
Phe Arg Tyr Glu Asn Asn Pro Phe Leu Gly Phe Ala Gly Ala Ile Gly
100 105 110 tac tca atg aat gga cca aga ata gag ttc gaa gta tcc tat gaa act 384
Tyr Ser Met Asn Gly Pro Arg Ile Glu Phe Glu Val Ser Tyr Glu Thr
115 120 125 ttt gat gta aaa aac cta ggt ggc aac tat aaa aac aac gca cac atg 432
Phe Asp Val Lys Asn Leu Gly Gly Asn Tyr Lys Asn Asn Ala His Met
130 135 140 tac tgt gct tta gat aca gca gca caa aat agc act aat ggc gca gga 480
Tyr Cys Ala Leu Asp Thr Ala Ala Gln Asn Ser Thr Asn Gly Ala Gly
145 150 155 160 tta act aca tct gtt atg gta aaa aac gaa aat tta aca aat ata tca 528
Leu Thr Thr Ser Val Met Val Lys Asn Glu Asn Leu Thr Asn Ile Ser
165 170 175 tta atg tta aat gcg tgt tat gat atc atg ctt gat gga ata cca gtt 576
Leu Met Leu Asn Ala Cys Tyr Asp Ile Met Leu Asp Gly Ile Pro Val
180 185 190 tct cca tat gta tgt gca ggt att ggc act gac tta gtg tca gta att 624
Ser Pro Tyr Val Cys Ala Gly Ile Gly Thr Asp Leu Val Ser Val Ile
195 200 205 aat gct aca aat cct aaa tta tct tat caa gga aag cta ggc ata agt 672
Asn Ala Thr Asn Pro Lys Leu Ser Tyr Gln Gly Lys Leu Gly Ile Ser
210 215 220 tac tca atc aat tct gaa gct tct atc ttt atc ggt gga cat ttc cat 720
Tyr Ser Ile Asn Ser Glu Ala Ser Ile Phe Ile Gly Gly His Phe His
225 230 235 240 aga gtt ata ggt aat gaa ttt aaa gat att gct acc tta aaa ata ttt 768
Arg Val Ile Gly Asn Glu Phe Lys Asp Ile Ala Thr Leu Lys Ile Phe
245 250 255 act tca aaa aca gga ata tct aat cct ggc ttt gca tca gca aca ctt 816
Thr Ser Lys Thr Gly Ile Ser Asn Pro Gly Phe Ala Ser Ala Thr Leu
260 265 270 gat gtt tgt cac ttt ggt ata gaa att gga gga agg ttt gta ttt taa 864
Asp Val Cys His Phe Gly Ile Glu Ile Gly Gly Arg Phe Val Phe
275 280 285

-continued

<210> SEQ ID NO 2
<211> LENGTH: 287
<212> TYPE: PRT
<213> ORGANISM: Cowdria ruminantium

<400> SEQUENCE: 2

```
Met Asn Cys Lys Lys Ile Phe Ile Thr Ser Thr Leu Ile Ser Leu Val
  1               5                  10                  15

Ser Phe Leu Pro Gly Val Ser Phe Ser Asp Val Ile Gln Glu Asp Ser
             20                  25                  30

Asn Pro Ala Gly Ser Val Tyr Ile Ser Ala Lys Tyr Met Pro Thr Ala
         35                  40                  45

Ser His Phe Gly Lys Met Ser Ile Lys Glu Asp Ser Lys Asn Thr Gln
     50                  55                  60

Thr Val Phe Gly Leu Lys Lys Asp Trp Asp Gly Val Lys Thr Pro Ser
 65                  70                  75                  80

Asp Ser Ser Asn Thr Asn Ser Thr Ile Phe Thr Glu Lys Asp Tyr Ser
                 85                  90                  95

Phe Arg Tyr Glu Asn Asn Pro Phe Leu Gly Phe Ala Gly Ala Ile Gly
            100                 105                 110

Tyr Ser Met Asn Gly Pro Arg Ile Glu Phe Glu Val Ser Tyr Glu Thr
        115                 120                 125

Phe Asp Val Lys Asn Leu Gly Gly Asn Tyr Lys Asn Asn Ala His Met
    130                 135                 140

Tyr Cys Ala Leu Asp Thr Ala Ala Gln Asn Ser Thr Asn Gly Ala Gly
145                 150                 155                 160

Leu Thr Thr Ser Val Met Val Lys Asn Glu Asn Leu Thr Asn Ile Ser
                165                 170                 175

Leu Met Leu Asn Ala Cys Tyr Asp Ile Met Leu Asp Gly Ile Pro Val
            180                 185                 190

Ser Pro Tyr Val Cys Ala Gly Ile Gly Thr Asp Leu Val Ser Val Ile
        195                 200                 205

Asn Ala Thr Asn Pro Lys Leu Ser Tyr Gln Gly Lys Leu Gly Ile Ser
    210                 215                 220

Tyr Ser Ile Asn Ser Glu Ala Ser Ile Phe Ile Gly Gly His Phe His
225                 230                 235                 240

Arg Val Ile Gly Asn Glu Phe Lys Asp Ile Ala Thr Leu Lys Ile Phe
                245                 250                 255

Thr Ser Lys Thr Gly Ile Ser Asn Pro Gly Phe Ala Ser Ala Thr Leu
            260                 265                 270

Asp Val Cys His Phe Gly Ile Glu Ile Gly Gly Arg Phe Val Phe
        275                 280                 285
```

<210> SEQ ID NO 3
<211> LENGTH: 842
<212> TYPE: DNA
<213> ORGANISM: Ehrlichia chaffeensis
<220> FEATURE:
<221> NAME/KEY: CDS
<222> LOCATION: (1)..(840)

<400> SEQUENCE: 3

```
atg aat tac aaa aaa agt ttc ata aca gcg att gat atc att aat atc       48
Met Asn Tyr Lys Lys Ser Phe Ile Thr Ala Ile Asp Ile Ile Asn Ile
  1               5                  10                  15

ctt ctc tta cct gga gta tca ttt tcc gac cca agg cag gta gtg gtc       96
```

-continued

```
Leu Leu Leu Pro Gly Val Ser Phe Ser Asp Pro Arg Gln Val Val Val
             20                  25                  30

att aac ggt aat ttc tac atc agt gga aaa tac gat gcc aag gct tcg      144
Ile Asn Gly Asn Phe Tyr Ile Ser Gly Lys Tyr Asp Ala Lys Ala Ser
        35                  40                  45

cat ttt gga gta ttc tct gct aag gaa gaa aga aat aca aca gtt gga      192
His Phe Gly Val Phe Ser Ala Lys Glu Glu Arg Asn Thr Thr Val Gly
    50                  55                  60

gtg ttt gga ctg aag caa aat tgg gac gga agc gca ata tcc aac tcc      240
Val Phe Gly Leu Lys Gln Asn Trp Asp Gly Ser Ala Ile Ser Asn Ser
 65                  70                  75                  80

tcc cca aac gat gta ttc act gtc tca aat tat tca ttt aaa tat gaa      288
Ser Pro Asn Asp Val Phe Thr Val Ser Asn Tyr Ser Phe Lys Tyr Glu
                 85                  90                  95

aac aac ccg ttt tta ggt ttt gca gga gct att ggt tac tca atg gat      336
Asn Asn Pro Phe Leu Gly Phe Ala Gly Ala Ile Gly Tyr Ser Met Asp
            100                 105                 110

ggt cca aga ata gag ctt gaa gta tct tat gaa aca ttt gat gta aaa      384
Gly Pro Arg Ile Glu Leu Glu Val Ser Tyr Glu Thr Phe Asp Val Lys
        115                 120                 125

aat caa ggt aac aat tat aag aat gaa gca cat aga tat tgt gct cta      432
Asn Gln Gly Asn Asn Tyr Lys Asn Glu Ala His Arg Tyr Cys Ala Leu
    130                 135                 140

tcc cat aac tca gca gca gac atg agt agt gca agt aat aat ttt gtc      480
Ser His Asn Ser Ala Ala Asp Met Ser Ser Ala Ser Asn Asn Phe Val
145                 150                 155                 160

ttt cta aaa aat gaa gga tta ctt gac ata tca ttt atg ctg aac gca      528
Phe Leu Lys Asn Glu Gly Leu Leu Asp Ile Ser Phe Met Leu Asn Ala
                165                 170                 175

tgc tat gac gta gta ggc gaa ggc ata cct ttt tct cct tat ata tgc      576
Cys Tyr Asp Val Val Gly Glu Gly Ile Pro Phe Ser Pro Tyr Ile Cys
            180                 185                 190

gca ggt atc ggt act gat tta gta tcc atg ttt gaa gct aca aat cct      624
Ala Gly Ile Gly Thr Asp Leu Val Ser Met Phe Glu Ala Thr Asn Pro
        195                 200                 205

aaa att tct tac caa gga aag tta ggt tta agc tac tct ata agc cca      672
Lys Ile Ser Tyr Gln Gly Lys Leu Gly Leu Ser Tyr Ser Ile Ser Pro
    210                 215                 220

gaa gct tct gtg ttt att ggt ggg cac ttt cat aag gta ata ggg aac      720
Glu Ala Ser Val Phe Ile Gly Gly His Phe His Lys Val Ile Gly Asn
225                 230                 235                 240

gaa ttt aga gat att cct act ata ata cct act gga tca aca ctt gca      768
Glu Phe Arg Asp Ile Pro Thr Ile Ile Pro Thr Gly Ser Thr Leu Ala
                245                 250                 255

gga aaa gga aac tac cct gca ata gta ata ctg gat gta tgc cac ttt      816
Gly Lys Gly Asn Tyr Pro Ala Ile Val Ile Leu Asp Val Cys His Phe
            260                 265                 270

gga ata gaa atg gga gga agg ttt aa                                   842
Gly Ile Glu Met Gly Gly Arg Phe
        275                 280


<210> SEQ ID NO 4
<211> LENGTH: 280
<212> TYPE: PRT
<213> ORGANISM: Ehrlichia chaffeensis

<400> SEQUENCE: 4

Met Asn Tyr Lys Lys Ser Phe Ile Thr Ala Ile Asp Ile Ile Asn Ile
  1               5                  10                  15

Leu Leu Leu Pro Gly Val Ser Phe Ser Asp Pro Arg Gln Val Val Val
```

-continued

```
            20                  25                  30

Ile Asn Gly Asn Phe Tyr Ile Ser Gly Lys Tyr Asp Ala Lys Ala Ser
        35                  40                  45

His Phe Gly Val Phe Ser Ala Lys Glu Glu Arg Asn Thr Thr Val Gly
    50                  55                  60

Val Phe Gly Leu Lys Gln Asn Trp Asp Gly Ser Ala Ile Ser Asn Ser
65                  70                  75                  80

Ser Pro Asn Asp Val Phe Thr Val Ser Asn Tyr Ser Phe Lys Tyr Glu
                85                  90                  95

Asn Asn Pro Phe Leu Gly Phe Ala Gly Ala Ile Gly Tyr Ser Met Asp
            100                 105                 110

Gly Pro Arg Ile Glu Leu Glu Val Ser Tyr Glu Thr Phe Asp Val Lys
        115                 120                 125

Asn Gln Gly Asn Asn Tyr Lys Asn Glu Ala His Arg Tyr Cys Ala Leu
    130                 135                 140

Ser His Asn Ser Ala Ala Asp Met Ser Ser Ala Ser Asn Asn Phe Val
145                 150                 155                 160

Phe Leu Lys Asn Glu Gly Leu Leu Asp Ile Ser Phe Met Leu Asn Ala
                165                 170                 175

Cys Tyr Asp Val Val Gly Glu Gly Ile Pro Phe Ser Pro Tyr Ile Cys
            180                 185                 190

Ala Gly Ile Gly Thr Asp Leu Val Ser Met Phe Glu Ala Thr Asn Pro
        195                 200                 205

Lys Ile Ser Tyr Gln Gly Lys Leu Gly Leu Ser Tyr Ser Ile Ser Pro
    210                 215                 220

Glu Ala Ser Val Phe Ile Gly Gly His Phe His Lys Val Ile Gly Asn
225                 230                 235                 240

Glu Phe Arg Asp Ile Pro Thr Ile Ile Pro Thr Gly Ser Thr Leu Ala
                245                 250                 255

Gly Lys Gly Asn Tyr Pro Ala Ile Val Ile Leu Asp Val Cys His Phe
            260                 265                 270

Gly Ile Glu Met Gly Gly Arg Phe
        275                 280


<210> SEQ ID NO 5
<211> LENGTH: 849
<212> TYPE: DNA
<213> ORGANISM: Anaplasma marginale
<220> FEATURE:
<221> NAME/KEY: CDS
<222> LOCATION: (1)..(846)

<400> SEQUENCE: 5

atg aat tac aga gaa ttg ttt aca ggg ggc ctg tca gca gcc aca gtc       48
Met Asn Tyr Arg Glu Leu Phe Thr Gly Gly Leu Ser Ala Ala Thr Val
  1               5                  10                  15

tgc gcc tgc tcc cta ctt gtt agt ggg gcc gta gtg gca tct ccc atg       96
Cys Ala Cys Ser Leu Leu Val Ser Gly Ala Val Val Ala Ser Pro Met
            20                  25                  30

agt cac gaa gtg gct tct gaa ggg gga gta atg gga ggt agc ttt tac      144
Ser His Glu Val Ala Ser Glu Gly Gly Val Met Gly Gly Ser Phe Tyr
        35                  40                  45

gtg ggt gcg gcc tac agc cca gca ttt cct tct gtt acc tcg ttc gac      192
Val Gly Ala Ala Tyr Ser Pro Ala Phe Pro Ser Val Thr Ser Phe Asp
    50                  55                  60

atg cgt gag tca agc aaa gag acc tca tac gtt aga ggc tat gac aag      240
Met Arg Glu Ser Ser Lys Glu Thr Ser Tyr Val Arg Gly Tyr Asp Lys
```

-continued

```
 65                  70                  75                  80

agc att gca acg att gat gtg agt gtg cca gca aac ttt tcc aaa tct      288
Ser Ile Ala Thr Ile Asp Val Ser Val Pro Ala Asn Phe Ser Lys Ser
                 85                  90                  95

ggc tac act ttt gcc ttc tct aaa aac tta atc acg tct ttc gac ggc      336
Gly Tyr Thr Phe Ala Phe Ser Lys Asn Leu Ile Thr Ser Phe Asp Gly
            100                 105                 110

gct gtg gga tat tct ctg gga gga gcc aga gtg gaa ttg gaa gcg agc      384
Ala Val Gly Tyr Ser Leu Gly Gly Ala Arg Val Glu Leu Glu Ala Ser
        115                 120                 125

tac aga agg ttt gct act ttg gcg gac ggg cag tac gca aaa agt ggt      432
Tyr Arg Arg Phe Ala Thr Leu Ala Asp Gly Gln Tyr Ala Lys Ser Gly
    130                 135                 140

gcg gaa tct ctg gca gct att acc cgc gac gct aac att act gag acc      480
Ala Glu Ser Leu Ala Ala Ile Thr Arg Asp Ala Asn Ile Thr Glu Thr
145                 150                 155                 160

aat tac ttc gta gtc aaa att gat gaa atc aca aac acc tca gtc atg      528
Asn Tyr Phe Val Val Lys Ile Asp Glu Ile Thr Asn Thr Ser Val Met
                165                 170                 175

tta aat ggc tgc tat gac gtg ctg cac aca gat tta cct gtg tcc ccg      576
Leu Asn Gly Cys Tyr Asp Val Leu His Thr Asp Leu Pro Val Ser Pro
            180                 185                 190

tat gta tgt gcc ggg ata ggc gca agc ttt gtt gac atc tct aag caa      624
Tyr Val Cys Ala Gly Ile Gly Ala Ser Phe Val Asp Ile Ser Lys Gln
        195                 200                 205

gta acc aca aag ctg gcc tac agg ggc aag gtt ggg att agc tac cag      672
Val Thr Thr Lys Leu Ala Tyr Arg Gly Lys Val Gly Ile Ser Tyr Gln
    210                 215                 220

ttt act ccg gaa ata tcc ttg gtg gca ggt ggg ttc tac cac ggg cta      720
Phe Thr Pro Glu Ile Ser Leu Val Ala Gly Gly Phe Tyr His Gly Leu
225                 230                 235                 240

ttt gat gag tct tac aag gac att ccc gca cac aac agt gta aag ttc      768
Phe Asp Glu Ser Tyr Lys Asp Ile Pro Ala His Asn Ser Val Lys Phe
                245                 250                 255

tct gga gaa gca aaa gcc tca gtc aaa gcg cat att gct gac tac ggc      816
Ser Gly Glu Ala Lys Ala Ser Val Lys Ala His Ile Ala Asp Tyr Gly
            260                 265                 270

ttt aac ctt gga gca aga ttc ctg ttc agc taa                          849
Phe Asn Leu Gly Ala Arg Phe Leu Phe Ser
        275                 280


<210> SEQ ID NO 6
<211> LENGTH: 282
<212> TYPE: PRT
<213> ORGANISM: Anaplasma marginale

<400> SEQUENCE: 6

Met Asn Tyr Arg Glu Leu Phe Thr Gly Gly Leu Ser Ala Ala Thr Val
  1               5                  10                  15

Cys Ala Cys Ser Leu Leu Val Ser Gly Ala Val Val Ala Ser Pro Met
             20                  25                  30

Ser His Glu Val Ala Ser Glu Gly Gly Val Met Gly Gly Ser Phe Tyr
         35                  40                  45

Val Gly Ala Ala Tyr Ser Pro Ala Phe Pro Ser Val Thr Ser Phe Asp
     50                  55                  60

Met Arg Glu Ser Ser Lys Glu Thr Ser Tyr Val Arg Gly Tyr Asp Lys
 65                  70                  75                  80

Ser Ile Ala Thr Ile Asp Val Ser Val Pro Ala Asn Phe Ser Lys Ser
                 85                  90                  95
```

-continued

Gly Tyr Thr Phe Ala Phe Ser Lys Asn Leu Ile Thr Ser Phe Asp Gly
100 105 110

Ala Val Gly Tyr Ser Leu Gly Gly Ala Arg Val Glu Leu Glu Ala Ser
115 120 125

Tyr Arg Arg Phe Ala Thr Leu Ala Asp Gly Gln Tyr Ala Lys Ser Gly
130 135 140

Ala Glu Ser Leu Ala Ala Ile Thr Arg Asp Ala Asn Ile Thr Glu Thr
145 150 155 160

Asn Tyr Phe Val Val Lys Ile Asp Glu Ile Thr Asn Thr Ser Val Met
165 170 175

Leu Asn Gly Cys Tyr Asp Val Leu His Thr Asp Leu Pro Val Ser Pro
180 185 190

Tyr Val Cys Ala Gly Ile Gly Ala Ser Phe Val Asp Ile Ser Lys Gln
195 200 205

Val Thr Thr Lys Leu Ala Tyr Arg Gly Lys Val Gly Ile Ser Tyr Gln
210 215 220

Phe Thr Pro Glu Ile Ser Leu Val Ala Gly Gly Phe Tyr His Gly Leu
225 230 235 240

Phe Asp Glu Ser Tyr Lys Asp Ile Pro Ala His Asn Ser Val Lys Phe
245 250 255

Ser Gly Glu Ala Lys Ala Ser Val Lys Ala His Ile Ala Asp Tyr Gly
260 265 270

Phe Asn Leu Gly Ala Arg Phe Leu Phe Ser
275 280

<210> SEQ ID NO 7
<211> LENGTH: 132
<212> TYPE: DNA
<213> ORGANISM: Ehrlichia chaffeensis

<400> SEQUENCE: 7
ggaatgaatt cagggacatt tctactctta aagcgtttgc tacaccatca tctgcagcta 60
ctccagactt agcaacagta acactgagtg tgtgtcactt tggagtagaa cttggaggaa 120
gatttaactt ct 132

<210> SEQ ID NO 8
<211> LENGTH: 861
<212> TYPE: DNA
<213> ORGANISM: Ehrlichia chaffeensis

<400> SEQUENCE: 8
atatgaactg cgaaaaattt tttataacaa ctgcattaac attactaatg tccttcttac 60
ctggaatatc actttctgat ccagtacagg atgacaacat tagtggtaat ttctacatca 120
gtggaaagta tatgccaagc gcttcgcatt ttggagtttt ttctgccaag gaagaaagaa 180
atacaacagt tggagtattt ggaatagagc aagattggga tagatgtgta atatctagaa 240
ccactttaag cgatatattc accgttccaa attattcatt taagtatgaa aataatctat 300
tttcaggatt tgcaggagct attggctact caatggatgg cccaagaata gagcttgaag 360
tatcttatga agcattcgat gttaaaaatc aaggtaacaa ttataagaac gaagcacata 420
gatattatgc tctgtcccat cttctcggca cagagacaca gatagatggt gcaggcagtg 480
cgtctgtctt tctaataaat gaaggactac ttgataaatc atttatgctg aacgcatgtt 540
atgatgtaat aagtgaaggc atacctttttt ctccttatat atgtgcaggt attggtattg 600

-continued

```
atttagtatc catgtttgaa gctataaatc ctaaaatttc ttatcaagga aaattaggct    660

taagttaccc tataagccca gaagcttctg tgtttattgg tggacatttt cataaggtga    720

taggaaacga atttagagat attcctacta tgatacctag tgaatcagcg cttgcaggaa    780

aaggaaacta ccctgcaata gtaacactgg acgtgttcta ctttggcata gaacttggag    840

gaaggtttaa cttccaactt t                                              861
```

<210> SEQ ID NO 9
<211> LENGTH: 837
<212> TYPE: DNA
<213> ORGANISM: Ehrlichia chaffeensis

<400> SEQUENCE: 9

```
atatgaattg caaaaaattt tttataacaa ctgcattagt atcactaatg tcctttctac     60

ctggaatatc attttctgat ccagtgcaag gtgacaatat tagtggtaat ttctatgtta    120

gtggcaagta tatgccaagt gcttcgcatt ttggcatgtt ttctgccaaa gaagaaaaaa    180

atcctactgt tgcattgtat ggcttaaaac aagattggga agggattagc tcatcaagtc    240

acaatgataa tcatttcaat aacaagggtt attcatttaa atatgaaaat aacccatttt    300

tagggtttgc aggagctatt ggttattcaa tgggtggtcc aagagtagag tttgaagtgt    360

cctatgaaac atttgacgtt aaaaatcagg gtaataacta taaaaatgat gctcacagat    420

actgtgcttt aggtcaacaa gacaacagcg gaatacctaa aactagtaaa tacgtactgt    480

taaaaagcga aggattgctt gacatatcat ttatgctaaa tgcatgctat gatataataa    540

acgagagcat acctttgtct ccttacatat gtgcaggtgt tggtactgat ttaatatcca    600

tgtttgaagc tacaaatcct aaaatttctt accaagggaa gttaggtcta agttactcta    660

taaacccaga agcttctgta tttattggtg gacattttca taaggtgata ggaaacgaat    720

ttagggacat tcctactctg aaagcatttg ttacgtcatc agctactcca gatctagcaa    780

tagtaacact aagtgtatgt cattttggaa tagaacttgg aggaaggttt aacttct       837
```

<210> SEQ ID NO 10
<211> LENGTH: 843
<212> TYPE: DNA
<213> ORGANISM: Ehrlichia chaffeensis

<400> SEQUENCE: 10

```
atatgaattg caaaaaattt tttataacaa ctacattagt atcgctaatg tccttcttac     60

ctggaatatc attttctgat gcagtacaga acgacaatgt tggtggtaat ttctatatca    120

gtgggaaata tgtaccaagt gtttcacatt ttggcgtatt ctctgctaaa caggaaagaa    180

atacaacaat cggagtattt ggattaaagc aagattggga tggcagcaca atatctaaaa    240

attctccaga aaatacattt aacgttccaa attattcatt taaatatgaa aataatccat    300

ttctaggttt tgcaggagct gttggttatt taatgaatgg tccaagaata gagttagaaa    360

tgtcctatga aacatttgat gtgaaaaacc agggtaataa ctataagaac gatgctcaca    420

aatattatgc tttaacccat aacagtgggg gaaagctaag caatgcaggt gataagtttg    480

tttttctaaa aaatgaagga ctacttgata tatcacttat gttgaatgca tgctatgatg    540

taataagtga aggaatacct ttctctcctt acatatgtgc aggtgttggt actgatttaa    600

tatccatgtt tgaagctata aaccctaaaa tttcttatca aggaaagtta ggtttgagtt    660

actccataag cccagaagct tctgtttttg ttggtggaca ttttcataag gtgataggga    720

atgaattcag agatattcct gctatgatac ccagtacctc aactctcaca ggtaatcact    780
```

-continued ttactatagt aacactaagt gtatgccact ttggagtgga acttggagga aggtttaact 840
ttt 843

<210> SEQ ID NO 11
<211> LENGTH: 830
<212> TYPE: DNA
<213> ORGANISM: Ehrlichia chaffeensis

<400> SEQUENCE: 11
atatgaatta caaaaaagtt ttcataacaa gtgcattgat atcattaata tcttctctac 60
ctggagtatc attttccgac ccagcaggta gtggtattaa cggtaatttc tacatcagtg 120
gaaaatacat gccaagtgct tcgcattttg gagtattctc tgctaaggaa gaaagaaata 180
caacagttgg agtgtttgga ctgaagcaaa attgggacgg aagcgcaata tccaactcct 240
ccccaaacga tgtattcact gtctcaaatt attcatttaa atatgaaaac aacccgtttt 300
taggttttgc aggagctatt ggttactcaa tggatggtcc aagaatagag cttgaagtat 360
cttatgaaac atttgatgta aaaaatcaag gtaacaatta taagaatgaa gcacatagat 420
attgtgctct atcccataac tcagcagcag acatgagtag tgcaagtaat aattttgtct 480
ttctaaaaaa tgaaggatta cttgacatat catttatgct gaacgcatgc tatgacgtag 540
taggcgaagg catacctttt tctccttata tatgcgcagg tatcggtact gatttagtat 600
ccatgtttga agctacaaat cctaaaattt cttaccaagg aaagttaggt ttaagctact 660
ctataagccc agaagcttct gtgtttattg gtgggcactt tcataaggta atagggaacg 720
aatttagaga tattcctact ataataccta ctggatcaac acttgcagga aaaggaaact 780
accctgcaat agtaatactg gatgtatgcc actttggaat agaaatggga 830

<210> SEQ ID NO 12
<211> LENGTH: 864
<212> TYPE: DNA
<213> ORGANISM: Ehrlichia canis

<400> SEQUENCE: 12
atatgaaata taaaaaaact tttacagtaa ctgcattagt attattaact tcctttacac 60
attttatacc tttttatagt ccagcacgtg ccagtacaat tcacaacttc tacattagtg 120
gaaaatatat gccaacagcg tcacattttg gaatttttttc agctaaagaa gaacaaagtt 180
ttactaaggt attagttggg ttagatcaac gattatcaca taatattata aacaataatg 240
atacagcaaa gagtcttaag gttcaaaatt attcatttaa atacaaaaat aacccatttc 300
taggatttgc aggagctatt ggttattcaa taggcaattc aagaatagaa ctagaagtat 360
cacatgaaat atttgatact aaaaacccag gaaacaatta tttaaatgac tctcacaaat 420
attgcgcttt atctcatgga agtcacatat gcagtgatgg aaatagcgga gattggtaca 480
ctgcaaaaac tgataagttt gtacttctga aaaatgaagg tttacttgac gtctcattta 540
tgttaaacgc atgttatgac ataacaactg aaaaaatgcc tttttcacct tatatatgtg 600
caggtattgg tactgatctc atatctatgt ttgagacaac acaaaacaaa atatcttatc 660
aaggaaagtt aggtttaaac tatactataa actcaagagt ttctgttttt gcaggtgggc 720
actttcataa ggtaataggt aatgaattta aaggtattcc tactctatta cctgatggat 780
caaacattaa agtacaacag tctgcaacag taacattaga tgtgtgccat ttcgggttag 840
agattggaag tagatttttc tttt 864

-continued

<210> SEQ ID NO 13
<211> LENGTH: 399
<212> TYPE: DNA
<213> ORGANISM: Ehrlichia canis

<400> SEQUENCE: 13

```
atatgaattg taaaaaagtt ttcacaataa gtgcattgat atcatccata tacttcctac     60

ctaatgtctc atactctaac ccagtatatg gtaacagtat gtatggtaat ttttacatat    120

caggaaagta catgccaagt gttcctcatt ttggaatttt ttcagctgaa gaagagaaaa    180

aaaagacaac tgtagtatat ggcttaaaag aaaactgggc aggagatgca atatctagtc    240

aaagtccaga tgataatttt accattcgaa attactcatt caagtatgca agcaacaagt    300

ttttagggtt tgcagtagct attggttact cgataggcag tccaagaata gaagttgaga    360

tgtcttatga agcatttgat gtaaaaaatc aaggtaaca                           399
```

<210> SEQ ID NO 14
<211> LENGTH: 43
<212> TYPE: PRT
<213> ORGANISM: Ehrlichia chaffeensis

<400> SEQUENCE: 14

```
Asn Glu Phe Arg Asp Ile Ser Thr Leu Lys Ala Phe Ala Thr Pro Ser
  1               5                  10                  15

Ser Ala Ala Thr Pro Asp Leu Ala Thr Val Thr Leu Ser Val Cys His
             20                  25                  30

Phe Gly Val Glu Leu Gly Gly Arg Phe Asn Phe
         35                  40
```

<210> SEQ ID NO 15
<211> LENGTH: 286
<212> TYPE: PRT
<213> ORGANISM: Ehrlichia chaffeensis

<400> SEQUENCE: 15

```
Met Asn Cys Glu Lys Phe Phe Ile Thr Thr Ala Leu Thr Leu Leu Met
  1               5                  10                  15

Ser Phe Leu Pro Gly Ile Ser Leu Ser Asp Pro Val Gln Asp Asp Asn
             20                  25                  30

Ile Ser Gly Asn Phe Tyr Ile Ser Gly Lys Tyr Met Pro Ser Ala Ser
         35                  40                  45

His Phe Gly Val Phe Ser Ala Lys Glu Glu Arg Asn Thr Thr Val Gly
     50                  55                  60

Val Phe Gly Ile Glu Gln Asp Trp Asp Arg Cys Val Ile Ser Arg Thr
 65                  70                  75                  80

Thr Leu Ser Asp Ile Phe Thr Val Pro Asn Tyr Ser Phe Lys Tyr Glu
                 85                  90                  95

Asn Asn Leu Phe Ser Gly Phe Ala Gly Ala Ile Gly Tyr Ser Met Asp
            100                 105                 110

Gly Pro Arg Ile Glu Leu Glu Val Ser Tyr Glu Ala Phe Asp Val Lys
        115                 120                 125

Asn Gln Gly Asn Asn Tyr Lys Asn Glu Ala His Arg Tyr Tyr Ala Leu
    130                 135                 140

Ser His Leu Leu Gly Thr Glu Thr Gln Ile Asp Gly Ala Gly Ser Ala
145                 150                 155                 160

Ser Val Phe Leu Ile Asn Glu Gly Leu Leu Asp Lys Ser Phe Met Leu
                165                 170                 175
```

-continued

```
Asn Ala Cys Tyr Asp Val Ile Ser Glu Gly Ile Pro Phe Ser Pro Tyr
            180                 185                 190

Ile Cys Ala Gly Ile Gly Ile Asp Leu Val Ser Met Phe Glu Ala Ile
        195                 200                 205

Asn Pro Lys Ile Ser Tyr Gln Gly Lys Leu Gly Leu Ser Tyr Pro Ile
    210                 215                 220

Ser Pro Glu Ala Ser Val Phe Ile Gly Gly His Phe His Lys Val Ile
225                 230                 235                 240

Gly Asn Glu Phe Arg Asp Ile Pro Thr Met Ile Pro Ser Glu Ser Ala
                245                 250                 255

Leu Ala Gly Lys Gly Asn Tyr Pro Ala Ile Val Thr Leu Asp Val Phe
            260                 265                 270

Tyr Phe Gly Ile Glu Leu Gly Gly Arg Phe Asn Phe Gln Leu
        275                 280                 285


<210> SEQ ID NO 16
<211> LENGTH: 278
<212> TYPE: PRT
<213> ORGANISM: Ehrlichia chaffeensis

<400> SEQUENCE: 16

Met Asn Cys Lys Lys Phe Phe Ile Thr Thr Ala Leu Val Ser Leu Met
  1               5                  10                  15

Ser Phe Leu Pro Gly Ile Ser Phe Ser Asp Pro Val Gln Gly Asp Asn
             20                  25                  30

Ile Ser Gly Asn Phe Tyr Val Ser Gly Lys Tyr Met Pro Ser Ala Ser
         35                  40                  45

His Phe Gly Met Phe Ser Ala Lys Glu Glu Lys Asn Pro Thr Val Ala
     50                  55                  60

Leu Tyr Gly Leu Lys Gln Asp Trp Glu Gly Ile Ser Ser Ser Ser His
 65                  70                  75                  80

Asn Asp Asn His Phe Asn Asn Lys Gly Tyr Ser Phe Lys Tyr Glu Asn
                 85                  90                  95

Asn Pro Phe Leu Gly Phe Ala Gly Ala Ile Gly Tyr Ser Met Gly Gly
            100                 105                 110

Pro Arg Val Glu Phe Glu Val Ser Tyr Glu Thr Phe Asp Val Lys Asn
        115                 120                 125

Gln Gly Asn Asn Tyr Lys Asn Asp Ala His Arg Tyr Cys Ala Leu Gly
    130                 135                 140

Gln Gln Asp Asn Ser Gly Ile Pro Lys Thr Ser Lys Tyr Val Leu Leu
145                 150                 155                 160

Lys Ser Glu Gly Leu Leu Asp Ile Ser Phe Met Leu Asn Ala Cys Tyr
                165                 170                 175

Asp Ile Ile Asn Glu Ser Ile Pro Leu Ser Pro Tyr Ile Cys Ala Gly
            180                 185                 190

Val Gly Thr Asp Leu Ile Ser Met Phe Glu Ala Thr Asn Pro Lys Ile
        195                 200                 205

Ser Tyr Gln Gly Lys Leu Gly Leu Ser Tyr Ser Ile Asn Pro Glu Ala
    210                 215                 220

Ser Val Phe Ile Gly Gly His Phe His Lys Val Ile Gly Asn Glu Phe
225                 230                 235                 240

Arg Asp Ile Pro Thr Leu Lys Ala Phe Val Thr Ser Ser Ala Thr Pro
                245                 250                 255

Asp Leu Ala Ile Val Thr Leu Ser Val Cys His Phe Gly Ile Glu Leu
```

-continued

```
        260                 265                 270

Gly Gly Arg Phe Asn Phe
        275


<210> SEQ ID NO 17
<211> LENGTH: 280
<212> TYPE: PRT
<213> ORGANISM: Ehrlichia chaffeensis

<400> SEQUENCE: 17

Met Asn Cys Lys Lys Phe Phe Ile Thr Thr Thr Leu Val Ser Leu Met
  1               5                  10                  15

Ser Phe Leu Pro Gly Ile Ser Phe Ser Asp Ala Val Gln Asn Asp Asn
             20                  25                  30

Val Gly Gly Asn Phe Tyr Ile Ser Gly Lys Tyr Val Pro Ser Val Ser
         35                  40                  45

His Phe Gly Val Phe Ser Ala Lys Gln Glu Arg Asn Thr Thr Ile Gly
     50                  55                  60

Val Phe Gly Leu Lys Gln Asp Trp Asp Gly Ser Thr Ile Ser Lys Asn
 65                  70                  75                  80

Ser Pro Glu Asn Thr Phe Asn Val Pro Asn Tyr Ser Phe Lys Tyr Glu
                 85                  90                  95

Asn Asn Pro Phe Leu Gly Phe Ala Gly Ala Val Gly Tyr Leu Met Asn
            100                 105                 110

Gly Pro Arg Ile Glu Leu Glu Met Ser Tyr Glu Thr Phe Asp Val Lys
        115                 120                 125

Asn Gln Gly Asn Asn Tyr Lys Asn Asp Ala His Lys Tyr Tyr Ala Leu
    130                 135                 140

Thr His Asn Ser Gly Gly Lys Leu Ser Asn Ala Gly Asp Lys Phe Val
145                 150                 155                 160

Phe Leu Lys Asn Glu Gly Leu Leu Asp Ile Ser Leu Met Leu Asn Ala
                165                 170                 175

Cys Tyr Asp Val Ile Ser Glu Gly Ile Pro Phe Ser Pro Tyr Ile Cys
            180                 185                 190

Ala Gly Val Gly Thr Asp Leu Ile Ser Met Phe Glu Ala Ile Asn Pro
        195                 200                 205

Lys Ile Ser Tyr Gln Gly Lys Leu Gly Leu Ser Tyr Ser Ile Ser Pro
    210                 215                 220

Glu Ala Ser Val Phe Val Gly Gly His Phe His Lys Val Ile Gly Asn
225                 230                 235                 240

Glu Phe Arg Asp Ile Pro Ala Met Ile Pro Ser Thr Ser Thr Leu Thr
                245                 250                 255

Gly Asn His Phe Thr Ile Val Thr Leu Ser Val Cys His Phe Gly Val
            260                 265                 270

Glu Leu Gly Gly Arg Phe Asn Phe
        275                 280


<210> SEQ ID NO 18
<211> LENGTH: 276
<212> TYPE: PRT
<213> ORGANISM: Ehrlichia chaffeensis

<400> SEQUENCE: 18

Met Asn Tyr Lys Lys Val Phe Ile Thr Ser Ala Leu Ile Ser Leu Ile
  1               5                  10                  15

Ser Ser Leu Pro Gly Val Ser Phe Ser Asp Pro Ala Gly Ser Gly Ile
```

-continued

```
            20                  25                  30

Asn Gly Asn Phe Tyr Ile Ser Gly Lys Tyr Met Pro Ser Ala Ser His
        35                  40                  45

Phe Gly Val Phe Ser Ala Lys Glu Glu Arg Asn Thr Thr Val Gly Val
    50                  55                  60

Phe Gly Leu Lys Gln Asn Trp Asp Gly Ser Ala Ile Ser Asn Ser Ser
 65                  70                  75                  80

Pro Asn Asp Val Phe Thr Val Ser Asn Tyr Ser Phe Lys Tyr Glu Asn
                85                  90                  95

Asn Pro Phe Leu Gly Phe Ala Gly Ala Ile Gly Tyr Ser Met Asp Gly
            100                 105                 110

Pro Arg Ile Glu Leu Glu Val Ser Tyr Glu Thr Phe Asp Val Lys Asn
        115                 120                 125

Gln Gly Asn Asn Tyr Lys Asn Glu Ala His Arg Tyr Cys Ala Leu Ser
    130                 135                 140

His Asn Ser Ala Ala Asp Met Ser Ser Ala Ser Asn Asn Phe Val Phe
145                 150                 155                 160

Leu Lys Asn Glu Gly Leu Leu Asp Ile Ser Phe Met Leu Asn Ala Cys
                165                 170                 175

Tyr Asp Val Val Gly Glu Gly Ile Pro Phe Ser Pro Tyr Ile Cys Ala
            180                 185                 190

Gly Ile Gly Thr Asp Leu Val Ser Met Phe Glu Ala Thr Asn Pro Lys
        195                 200                 205

Ile Ser Tyr Gln Gly Lys Leu Gly Leu Ser Tyr Ser Ile Ser Pro Glu
    210                 215                 220

Ala Ser Val Phe Ile Gly Gly His Phe His Lys Val Ile Gly Asn Glu
225                 230                 235                 240

Phe Arg Asp Ile Pro Thr Ile Ile Pro Thr Gly Ser Thr Leu Ala Gly
                245                 250                 255

Lys Gly Asn Tyr Pro Ala Ile Val Ile Leu Asp Val Cys His Phe Gly
            260                 265                 270

Ile Glu Met Gly
        275


<210> SEQ ID NO 19
<211> LENGTH: 287
<212> TYPE: PRT
<213> ORGANISM: Ehrlichia canis

<400> SEQUENCE: 19

Met Lys Tyr Lys Lys Thr Phe Thr Val Thr Ala Leu Val Leu Leu Thr
  1               5                  10                  15

Ser Phe Thr His Phe Ile Pro Phe Tyr Ser Pro Ala Arg Ala Ser Thr
            20                  25                  30

Ile His Asn Phe Tyr Ile Ser Gly Lys Tyr Met Pro Thr Ala Ser His
        35                  40                  45

Phe Gly Ile Phe Ser Ala Lys Glu Glu Gln Ser Phe Thr Lys Val Leu
    50                  55                  60

Val Gly Leu Asp Gln Arg Leu Ser His Asn Ile Ile Asn Asn Asn Asp
 65                  70                  75                  80

Thr Ala Lys Ser Leu Lys Val Gln Asn Tyr Ser Phe Lys Tyr Lys Asn
                85                  90                  95

Asn Pro Phe Leu Gly Phe Ala Gly Ala Ile Gly Tyr Ser Ile Gly Asn
            100                 105                 110
```

-continued

```
Ser Arg Ile Glu Leu Glu Val Ser His Glu Ile Phe Asp Thr Lys Asn
        115                 120                 125

Pro Gly Asn Asn Tyr Leu Asn Asp Ser His Lys Tyr Cys Ala Leu Ser
    130                 135                 140

His Gly Ser His Ile Cys Ser Asp Gly Asn Ser Gly Asp Trp Tyr Thr
145                 150                 155                 160

Ala Lys Thr Asp Lys Phe Val Leu Leu Lys Asn Glu Gly Leu Leu Asp
                165                 170                 175

Val Ser Phe Met Leu Asn Ala Cys Tyr Asp Ile Thr Thr Glu Lys Met
            180                 185                 190

Pro Phe Ser Pro Tyr Ile Cys Ala Gly Ile Gly Thr Asp Leu Ile Ser
        195                 200                 205

Met Phe Glu Thr Thr Gln Asn Lys Ile Ser Tyr Gln Gly Lys Leu Gly
    210                 215                 220

Leu Asn Tyr Thr Ile Asn Ser Arg Val Ser Val Phe Ala Gly Gly His
225                 230                 235                 240

Phe His Lys Val Ile Gly Asn Glu Phe Lys Gly Ile Pro Thr Leu Leu
                245                 250                 255

Pro Asp Gly Ser Asn Ile Lys Val Gln Gln Ser Ala Thr Val Thr Leu
            260                 265                 270

Asp Val Cys His Phe Gly Leu Glu Ile Gly Ser Arg Phe Phe Phe
        275                 280                 285


<210> SEQ ID NO 20
<211> LENGTH: 133
<212> TYPE: PRT
<213> ORGANISM: Ehrlichia canis

<400> SEQUENCE: 20

Met Asn Cys Lys Lys Val Phe Thr Ile Ser Ala Leu Ile Ser Ser Ile
  1               5                  10                  15

Tyr Phe Leu Pro Asn Val Ser Tyr Ser Asn Pro Val Tyr Gly Asn Ser
            20                  25                  30

Met Tyr Gly Asn Phe Tyr Ile Ser Gly Lys Tyr Met Pro Ser Val Pro
        35                  40                  45

His Phe Gly Ile Phe Ser Ala Glu Glu Glu Lys Lys Lys Thr Thr Val
     50                  55                  60

Val Tyr Gly Leu Lys Glu Asn Trp Ala Gly Asp Ala Ile Ser Ser Gln
 65                  70                  75                  80

Ser Pro Asp Asp Asn Phe Thr Ile Arg Asn Tyr Ser Phe Lys Tyr Ala
                 85                  90                  95

Ser Asn Lys Phe Leu Gly Phe Ala Val Ala Ile Gly Tyr Ser Ile Gly
            100                 105                 110

Ser Pro Arg Ile Glu Val Glu Met Ser Tyr Glu Ala Phe Asp Val Lys
        115                 120                 125

Asn Gln Gly Asn Asn
    130


<210> SEQ ID NO 21
<211> LENGTH: 686
<212> TYPE: DNA
<213> ORGANISM: Ehrlichia canis

<400> SEQUENCE: 21

atgaaagcta tcaaattcat acttaatgtc tgcttactat ttgcagcaat atttttaggg      60

tattcctata ttacaaaaca aggcatattt caaacaaaac atcatgatac acctaatact     120
```

-continued actataccaa atgaagacgg tattcaatct agctttagct taatcaatca agacggtaaa 180
acagtaacca gccaagattt cctagggaaa cacatgttag ttttgtttgg attctctgca 240
tgtaaaagca tttgccctgc agaattggga ttagtatctg aagcacttgc acaacttggt 300
aataatgcag acaaattaca agtaattttt attacaattg atccaaaaaa tgatactgta 360
gaaaaattaa aagaatttca tgaacatttt gattcaagaa ttcaaatgtt aacaggaaat 420
actgaagaca ttaatcaaat aattaaaaat tataaaatat atgttggaca agcagataaa 480
gatcatcaaa ttaaccattc tgcaataatg taccttattg acaaaaaagg atcatatctt 540
tcacacttca ttccagattt aaaatcacaa gaaaatcaag tagataagtt actatcttta 600
gttaagcagt atctgtaaat aaattcatgg aatacgttgg atgagtaggt ttttttttagt 660 atttttagtg ctaataacat tggcat 686

<210> SEQ ID NO 22
<211> LENGTH: 618
<212> TYPE: DNA
<213> ORGANISM: Ehrlichia chaffeensis

<400> SEQUENCE: 22
atgaaagtta tcaaatttat acttaatatc tgtttattat ttgcagcaat ttttctagga 60
tattcctacg taacaaaaca aggcattttt caagtaagag atcataacac tcccaataca 120
aatatatcaa ataaagccag cattactact agtttttcgt tagtaaatca agatggaaat 180
acagtaaata gtcaagattt tttgggaaaa tacatgctag ttttatttgg attttcttca 240
tgtaaaagca tctgccctgc tgaattagga atagcatctg aagttctctc acagcttggt 300
aatgacacag acaagttaca agtaattttc attacaattg atccaacaaa tgatactgta 360
caaaaattaa aaacatttca tgaacatttt gatcctagaa ttcaaatgct aacaggcagt 420
gcagaagata ttgaaaaaat aataaaaaat tacaaaatat atgttggaca agcagataaa 480
gataatcaaa ttgatcactc tgccataatg tacattatcg ataaaaaagg agaatacatt 540
tcacactttt ctccagattt aaaatcaaca gaaaatcaag tagataagtt actatctata 600
ataaaacaat atctctaa 618

<210> SEQ ID NO 23
<211> LENGTH: 205
<212> TYPE: PRT
<213> ORGANISM: Ehrlichia canis

<400> SEQUENCE: 23

Met Lys Ala Ile Lys Phe Ile Leu Asn Val Cys Leu Leu Phe Ala Ala
1 5 10 15

Ile Phe Leu Gly Tyr Ser Tyr Ile Thr Lys Gln Gly Ile Phe Gln Thr
20 25 30

Lys His His Asp Thr Pro Asn Thr Thr Ile Pro Asn Glu Asp Gly Ile
35 40 45

Gln Ser Ser Phe Ser Leu Ile Asn Gln Asp Gly Lys Thr Val Thr Ser
50 55 60

Gln Asp Phe Leu Gly Lys His Met Leu Val Leu Phe Gly Phe Ser Ala
65 70 75 80

Cys Lys Ser Ile Cys Pro Ala Glu Leu Gly Leu Val Ser Glu Ala Leu
85 90 95

Ala Gln Leu Gly Asn Asn Ala Asp Lys Leu Gln Val Ile Phe Ile Thr
100 105 110

-continued

```
Ile Asp Pro Lys Asn Asp Thr Val Glu Lys Leu Lys Glu Phe His Glu
        115                 120                 125

His Phe Asp Ser Arg Ile Gln Met Leu Thr Gly Asn Thr Glu Asp Ile
    130                 135                 140

Asn Gln Ile Ile Lys Asn Tyr Lys Ile Tyr Val Gly Gln Ala Asp Lys
145                 150                 155                 160

Asp His Gln Ile Asn His Ser Ala Ile Met Tyr Leu Ile Asp Lys Lys
                165                 170                 175

Gly Ser Tyr Leu Ser His Phe Ile Pro Asp Leu Lys Ser Gln Glu Asn
            180                 185                 190

Gln Val Asp Lys Leu Leu Ser Leu Val Lys Gln Tyr Leu
        195                 200                 205


<210> SEQ ID NO 24
<211> LENGTH: 205
<212> TYPE: PRT
<213> ORGANISM: Ehrlichia chaffeensis

<400> SEQUENCE: 24

Met Lys Val Ile Lys Phe Ile Leu Asn Ile Cys Leu Leu Phe Ala Ala
  1               5                  10                  15

Ile Phe Leu Gly Tyr Ser Tyr Val Thr Lys Gln Gly Ile Phe Gln Val
             20                  25                  30

Arg Asp His Asn Thr Pro Asn Thr Asn Ile Ser Asn Lys Ala Ser Ile
         35                  40                  45

Thr Thr Ser Phe Ser Leu Val Asn Gln Asp Gly Asn Thr Val Asn Ser
     50                  55                  60

Gln Asp Phe Leu Gly Lys Tyr Met Leu Val Leu Phe Gly Phe Ser Ser
 65                  70                  75                  80

Cys Lys Ser Ile Cys Pro Ala Glu Leu Gly Ile Ala Ser Glu Val Leu
                 85                  90                  95

Ser Gln Leu Gly Asn Asp Thr Asp Lys Leu Gln Val Ile Phe Ile Thr
            100                 105                 110

Ile Asp Pro Thr Asn Asp Thr Val Gln Lys Leu Lys Thr Phe His Glu
        115                 120                 125

His Phe Asp Pro Arg Ile Gln Met Leu Thr Gly Ser Ala Glu Asp Ile
    130                 135                 140

Glu Lys Ile Ile Lys Asn Tyr Lys Ile Tyr Val Gly Gln Ala Asp Lys
145                 150                 155                 160

Asp Asn Gln Ile Asp His Ser Ala Ile Met Tyr Ile Ile Asp Lys Lys
                165                 170                 175

Gly Glu Tyr Ile Ser His Phe Ser Pro Asp Leu Lys Ser Thr Glu Asn
            180                 185                 190

Gln Val Asp Lys Leu Leu Ser Ile Ile Lys Gln Tyr Leu
        195                 200                 205


<210> SEQ ID NO 25
<211> LENGTH: 618
<212> TYPE: DNA
<213> ORGANISM: Cowdria ruminantium
<220> FEATURE:
<221> NAME/KEY: CDS
<222> LOCATION: (1)..(615)

<400> SEQUENCE: 25

atg aag gct atc aag ttt ata ctt aat cta tgt tta cta ttt gca gca       48
Met Lys Ala Ile Lys Phe Ile Leu Asn Leu Cys Leu Leu Phe Ala Ala
```

-continued

```
  1               5                   10                  15

att ttt ttg gga tat tct tac ata aca aaa caa ggt ata ttc caa cca        96
Ile Phe Leu Gly Tyr Ser Tyr Ile Thr Lys Gln Gly Ile Phe Gln Pro
            20                  25                  30

aaa tta cac gac tct cct gat gtt aat ata tcg aac aaa gcg gat ata       144
Lys Leu His Asp Ser Pro Asp Val Asn Ile Ser Asn Lys Ala Asp Ile
        35                  40                  45

aat act agc ttt agc tta att aat cag gat ggt att acg ata tct agt       192
Asn Thr Ser Phe Ser Leu Ile Asn Gln Asp Gly Ile Thr Ile Ser Ser
     50                  55                  60

aaa gac ttc ctt gga aaa cat atg tta gtc ctt ttt ggg ttt tct tct       240
Lys Asp Phe Leu Gly Lys His Met Leu Val Leu Phe Gly Phe Ser Ser
 65                  70                  75                  80

tgt aaa act att tgc ccc atg gaa cta ggg tta gca tcc aca att cta       288
Cys Lys Thr Ile Cys Pro Met Glu Leu Gly Leu Ala Ser Thr Ile Leu
                85                  90                  95

gat caa ctt ggc aac gaa tct gac aag tta caa gta gtc ttt ata act       336
Asp Gln Leu Gly Asn Glu Ser Asp Lys Leu Gln Val Val Phe Ile Thr
            100                 105                 110

att gat cca aca aaa gat act gta gaa aca cta aaa gag ttt cac aaa       384
Ile Asp Pro Thr Lys Asp Thr Val Glu Thr Leu Lys Glu Phe His Lys
        115                 120                 125

aat ttt gac tca cgg att caa atg tta aca gga aac att gaa gct att       432
Asn Phe Asp Ser Arg Ile Gln Met Leu Thr Gly Asn Ile Glu Ala Ile
    130                 135                 140

aat caa ata gta caa ggg tac aaa gta tat gta ggt cag cca gac aat       480
Asn Gln Ile Val Gln Gly Tyr Lys Val Tyr Val Gly Gln Pro Asp Asn
145                 150                 155                 160

gat aac caa att aac cat tct gga ata atg tat att gta gac aag aaa       528
Asp Asn Gln Ile Asn His Ser Gly Ile Met Tyr Ile Val Asp Lys Lys
                165                 170                 175

gga gaa tat tta aca cat ttt gta cca gat tta aag tca aaa gag cct       576
Gly Glu Tyr Leu Thr His Phe Val Pro Asp Leu Lys Ser Lys Glu Pro
            180                 185                 190

caa gtg gat aaa tta ctt tct tta att aag cag tat ctt taa               618
Gln Val Asp Lys Leu Leu Ser Leu Ile Lys Gln Tyr Leu
        195                 200                 205


<210> SEQ ID NO 26
<211> LENGTH: 205
<212> TYPE: PRT
<213> ORGANISM: Cowdria ruminantium

<400> SEQUENCE: 26

Met Lys Ala Ile Lys Phe Ile Leu Asn Leu Cys Leu Leu Phe Ala Ala
  1               5                   10                  15

Ile Phe Leu Gly Tyr Ser Tyr Ile Thr Lys Gln Gly Ile Phe Gln Pro
            20                  25                  30

Lys Leu His Asp Ser Pro Asp Val Asn Ile Ser Asn Lys Ala Asp Ile
        35                  40                  45

Asn Thr Ser Phe Ser Leu Ile Asn Gln Asp Gly Ile Thr Ile Ser Ser
     50                  55                  60

Lys Asp Phe Leu Gly Lys His Met Leu Val Leu Phe Gly Phe Ser Ser
 65                  70                  75                  80

Cys Lys Thr Ile Cys Pro Met Glu Leu Gly Leu Ala Ser Thr Ile Leu
                85                  90                  95

Asp Gln Leu Gly Asn Glu Ser Asp Lys Leu Gln Val Val Phe Ile Thr
            100                 105                 110
```

-continued

```
Ile Asp Pro Thr Lys Asp Thr Val Glu Thr Leu Lys Glu Phe His Lys
        115                 120                 125

Asn Phe Asp Ser Arg Ile Gln Met Leu Thr Gly Asn Ile Glu Ala Ile
    130                 135                 140

Asn Gln Ile Val Gln Gly Tyr Lys Val Tyr Val Gly Gln Pro Asp Asn
145                 150                 155                 160

Asp Asn Gln Ile Asn His Ser Gly Ile Met Tyr Ile Val Asp Lys Lys
                165                 170                 175

Gly Glu Tyr Leu Thr His Phe Val Pro Asp Leu Lys Ser Lys Glu Pro
            180                 185                 190

Gln Val Asp Lys Leu Leu Ser Leu Ile Lys Gln Tyr Leu
        195                 200                 205


<210> SEQ ID NO 27
<211> LENGTH: 981
<212> TYPE: DNA
<213> ORGANISM: Cowdria ruminantium
<220> FEATURE:
<221> NAME/KEY: CDS
<222> LOCATION: (1)..(978)

<400> SEQUENCE: 27

atg aag aaa ata ttg gtt acg ttt tta gtt gtt gtt aat gtg ttt tgt       48
Met Lys Lys Ile Leu Val Thr Phe Leu Val Val Val Asn Val Phe Cys
  1               5                  10                  15

aat gct gcc att gct tca act gac tca tca gaa gat aaa cag tat att       96
Asn Ala Ala Ile Ala Ser Thr Asp Ser Ser Glu Asp Lys Gln Tyr Ile
             20                  25                  30

tta att ggt act ggt tct atg act gga gta tat tat cct ata gga ggt      144
Leu Ile Gly Thr Gly Ser Met Thr Gly Val Tyr Tyr Pro Ile Gly Gly
         35                  40                  45

agc ata tgt agg ttt att gca tct gat tat ggt aat gat aat aac agc      192
Ser Ile Cys Arg Phe Ile Ala Ser Asp Tyr Gly Asn Asp Asn Asn Ser
     50                  55                  60

ata gtt tgt tct ata tct tct aca act ggt agc gta tat aat ctt aat      240
Ile Val Cys Ser Ile Ser Ser Thr Thr Gly Ser Val Tyr Asn Leu Asn
 65                  70                  75                  80

tct atg cgt tat gca aat atg gat ata ggt att att caa tct gat tta      288
Ser Met Arg Tyr Ala Asn Met Asp Ile Gly Ile Ile Gln Ser Asp Leu
                 85                  90                  95

gag tac tat gca tat aat ggt att ggt tta tat gaa aaa atg cca gca      336
Glu Tyr Tyr Ala Tyr Asn Gly Ile Gly Leu Tyr Glu Lys Met Pro Ala
            100                 105                 110

atg agg cat cta aga ata tta tct tca tta cat aaa gaa tat ctt aca      384
Met Arg His Leu Arg Ile Leu Ser Ser Leu His Lys Glu Tyr Leu Thr
        115                 120                 125

att gtt gtt agg gcg aat tct aat ata tca gtt att gat gat ata aaa      432
Ile Val Val Arg Ala Asn Ser Asn Ile Ser Val Ile Asp Asp Ile Lys
    130                 135                 140

ggc aaa aga gtt aat att ggt agt cct ggt act ggt gta aga ata gca      480
Gly Lys Arg Val Asn Ile Gly Ser Pro Gly Thr Gly Val Arg Ile Ala
145                 150                 155                 160

atg tta aaa ttg tta aat gaa aaa gga tgg gga aga aaa gat ttt gct      528
Met Leu Lys Leu Leu Asn Glu Lys Gly Trp Gly Arg Lys Asp Phe Ala
                165                 170                 175

gtt atg gca gaa tta aaa tca tca gag caa gct caa gca tta tgt gat      576
Val Met Ala Glu Leu Lys Ser Ser Glu Gln Ala Gln Ala Leu Cys Asp
            180                 185                 190

aat aaa att gat gtg atg gta gat gtt gtt gga cat cct aat gct gca      624
Asn Lys Ile Asp Val Met Val Asp Val Val Gly His Pro Asn Ala Ala
```

-continued

```
        195                 200                 205

att caa gaa gca gca gca act tgt gat ata aaa ttt att tct tta gat      672
Ile Gln Glu Ala Ala Ala Thr Cys Asp Ile Lys Phe Ile Ser Leu Asp
    210                 215                 220

gat gat ctc ata gat aaa tta cat act aag tat ccc tat tat aaa agg      720
Asp Asp Leu Ile Asp Lys Leu His Thr Lys Tyr Pro Tyr Tyr Lys Arg
225                 230                 235                 240

gat att att agt ggt gcg tta tac agt aac tta cct gat ata caa act      768
Asp Ile Ile Ser Gly Ala Leu Tyr Ser Asn Leu Pro Asp Ile Gln Thr
                245                 250                 255

gtt tca gta aaa gct tct tta ata aca act act gaa tta agc aat gag      816
Val Ser Val Lys Ala Ser Leu Ile Thr Thr Thr Glu Leu Ser Asn Glu
            260                 265                 270

ttg gcc tat aaa gtt gtt aaa tct ttg gtt agc cat tta cat gaa cta      864
Leu Ala Tyr Lys Val Val Lys Ser Leu Val Ser His Leu His Glu Leu
        275                 280                 285

cat gga att act gga gct ctt aga aat ctt act gta aaa gac atg gta      912
His Gly Ile Thr Gly Ala Leu Arg Asn Leu Thr Val Lys Asp Met Val
    290                 295                 300

cag tca gat att aca cct tta cat gac ggt gca aaa cgt tat tat aag      960
Gln Ser Asp Ile Thr Pro Leu His Asp Gly Ala Lys Arg Tyr Tyr Lys
305                 310                 315                 320

gaa att gga gtt ata aaa taa                                          981
Glu Ile Gly Val Ile Lys
                325


<210> SEQ ID NO 28
<211> LENGTH: 326
<212> TYPE: PRT
<213> ORGANISM: Cowdria ruminantium

<400> SEQUENCE: 28

Met Lys Lys Ile Leu Val Thr Phe Leu Val Val Val Asn Val Phe Cys
  1               5                  10                  15

Asn Ala Ala Ile Ala Ser Thr Asp Ser Ser Glu Asp Lys Gln Tyr Ile
             20                  25                  30

Leu Ile Gly Thr Gly Ser Met Thr Gly Val Tyr Tyr Pro Ile Gly Gly
         35                  40                  45

Ser Ile Cys Arg Phe Ile Ala Ser Asp Tyr Gly Asn Asp Asn Asn Ser
     50                  55                  60

Ile Val Cys Ser Ile Ser Ser Thr Thr Gly Ser Val Tyr Asn Leu Asn
 65                  70                  75                  80

Ser Met Arg Tyr Ala Asn Met Asp Ile Gly Ile Ile Gln Ser Asp Leu
                 85                  90                  95

Glu Tyr Tyr Ala Tyr Asn Gly Ile Gly Leu Tyr Glu Lys Met Pro Ala
            100                 105                 110

Met Arg His Leu Arg Ile Leu Ser Ser Leu His Lys Glu Tyr Leu Thr
        115                 120                 125

Ile Val Val Arg Ala Asn Ser Asn Ile Ser Val Ile Asp Asp Ile Lys
    130                 135                 140

Gly Lys Arg Val Asn Ile Gly Ser Pro Gly Thr Gly Val Arg Ile Ala
145                 150                 155                 160

Met Leu Lys Leu Leu Asn Glu Lys Gly Trp Gly Arg Lys Asp Phe Ala
                165                 170                 175

Val Met Ala Glu Leu Lys Ser Ser Glu Gln Ala Gln Ala Leu Cys Asp
            180                 185                 190

Asn Lys Ile Asp Val Met Val Asp Val Val Gly His Pro Asn Ala Ala
```

-continued

```
        195                 200                 205

Ile Gln Glu Ala Ala Ala Thr Cys Asp Ile Lys Phe Ile Ser Leu Asp
    210                 215                 220

Asp Asp Leu Ile Asp Lys Leu His Thr Lys Tyr Pro Tyr Tyr Lys Arg
225                 230                 235                 240

Asp Ile Ile Ser Gly Ala Leu Tyr Ser Asn Leu Pro Asp Ile Gln Thr
                245                 250                 255

Val Ser Val Lys Ala Ser Leu Ile Thr Thr Thr Glu Leu Ser Asn Glu
            260                 265                 270

Leu Ala Tyr Lys Val Val Lys Ser Leu Val Ser His Leu His Glu Leu
        275                 280                 285

His Gly Ile Thr Gly Ala Leu Arg Asn Leu Thr Val Lys Asp Met Val
    290                 295                 300

Gln Ser Asp Ile Thr Pro Leu His Asp Gly Ala Lys Arg Tyr Tyr Lys
305                 310                 315                 320

Glu Ile Gly Val Ile Lys
                325


<210> SEQ ID NO 29
<211> LENGTH: 519
<212> TYPE: DNA
<213> ORGANISM: Cowdria ruminantium
<220> FEATURE:
<221> NAME/KEY: CDS
<222> LOCATION: (1)..(516)

<400> SEQUENCE: 29

atg aat ata ttc aat tat atg cag ata atg cct aat ata agt gtt gat       48
Met Asn Ile Phe Asn Tyr Met Gln Ile Met Pro Asn Ile Ser Val Asp
  1               5                  10                  15

gca ttt gtt gca cct act gct gta att ata ggt gat gtt tgt gta aat       96
Ala Phe Val Ala Pro Thr Ala Val Ile Ile Gly Asp Val Cys Val Asn
             20                  25                  30

gac aag tgt agc att tgg tat aac tca gta tta cgt gga gat gta ggc      144
Asp Lys Cys Ser Ile Trp Tyr Asn Ser Val Leu Arg Gly Asp Val Gly
         35                  40                  45

caa att gtt att ggt gta ggt act aat att caa gat ggg aca ata ata      192
Gln Ile Val Ile Gly Val Gly Thr Asn Ile Gln Asp Gly Thr Ile Ile
     50                  55                  60

cat gtt gat agg aaa tat ggt aat acg aat att ggc aaa aag gtt act      240
His Val Asp Arg Lys Tyr Gly Asn Thr Asn Ile Gly Lys Lys Val Thr
 65                  70                  75                  80

att ggg cat ggg tgt ata tta cat gct tgt gag ata caa gat tat gtg      288
Ile Gly His Gly Cys Ile Leu His Ala Cys Glu Ile Gln Asp Tyr Val
                 85                  90                  95

ctt gtt gga atg gga tct att att atg gat aac gtt gtg gtt gaa aag      336
Leu Val Gly Met Gly Ser Ile Ile Met Asp Asn Val Val Val Glu Lys
            100                 105                 110

aat gca atg gtg gct gct gga tca tta gtg gta aga ggt aaa gtt gtg      384
Asn Ala Met Val Ala Ala Gly Ser Leu Val Val Arg Gly Lys Val Val
        115                 120                 125

aaa act ggt gaa tta tgg gct ggt agg cct gca caa ttt tta aga atg      432
Lys Thr Gly Glu Leu Trp Ala Gly Arg Pro Ala Gln Phe Leu Arg Met
    130                 135                 140

ttg tct agt gat gaa att aaa gag ata agt aaa tct gct gat aac tat      480
Leu Ser Ser Asp Glu Ile Lys Glu Ile Ser Lys Ser Ala Asp Asn Tyr
145                 150                 155                 160

ata gag ctt gcc agt gat tac ata act ggt aag ttg taa                  519
Ile Glu Leu Ala Ser Asp Tyr Ile Thr Gly Lys Leu
```

-continued 165 170

<210> SEQ ID NO 30
<211> LENGTH: 172
<212> TYPE: PRT
<213> ORGANISM: Cowdria ruminantium

<400> SEQUENCE: 30

```
Met Asn Ile Phe Asn Tyr Met Gln Ile Met Pro Asn Ile Ser Val Asp
  1               5                  10                  15

Ala Phe Val Ala Pro Thr Ala Val Ile Ile Gly Asp Val Cys Val Asn
             20                  25                  30

Asp Lys Cys Ser Ile Trp Tyr Asn Ser Val Leu Arg Gly Asp Val Gly
         35                  40                  45

Gln Ile Val Ile Gly Val Gly Thr Asn Ile Gln Asp Gly Thr Ile Ile
     50                  55                  60

His Val Asp Arg Lys Tyr Gly Asn Thr Asn Ile Gly Lys Lys Val Thr
 65                  70                  75                  80

Ile Gly His Gly Cys Ile Leu His Ala Cys Glu Ile Gln Asp Tyr Val
                 85                  90                  95

Leu Val Gly Met Gly Ser Ile Ile Met Asp Asn Val Val Val Glu Lys
            100                 105                 110

Asn Ala Met Val Ala Ala Gly Ser Leu Val Val Arg Gly Lys Val Val
        115                 120                 125

Lys Thr Gly Glu Leu Trp Ala Gly Arg Pro Ala Gln Phe Leu Arg Met
    130                 135                 140

Leu Ser Ser Asp Glu Ile Lys Glu Ile Ser Lys Ser Ala Asp Asn Tyr
145                 150                 155                 160

Ile Glu Leu Ala Ser Asp Tyr Ile Thr Gly Lys Leu
                165                 170
```

<210> SEQ ID NO 31
<211> LENGTH: 753
<212> TYPE: DNA
<213> ORGANISM: Cowdria ruminantium
<220> FEATURE:
<221> NAME/KEY: CDS
<222> LOCATION: (1)..(750)

<400> SEQUENCE: 31

```
atg atg ata aga atc ttt ctt ttg tta ggc tta gta tta tta gta gca       48
Met Met Ile Arg Ile Phe Leu Leu Leu Gly Leu Val Leu Leu Val Ala
  1               5                  10                  15

agt ttt cca cta tta aat aac tgg cta tct aat cat tct ggt aag tct       96
Ser Phe Pro Leu Leu Asn Asn Trp Leu Ser Asn His Ser Gly Lys Ser
             20                  25                  30

act aca ttg gat aag gat gca gtt ata tct ata gtt gag gaa tat ata      144
Thr Thr Leu Asp Lys Asp Ala Val Ile Ser Ile Val Glu Glu Tyr Ile
         35                  40                  45

acc aat tat cct cag agg gta ata gat tta ctt act aca ggc caa gca      192
Thr Asn Tyr Pro Gln Arg Val Ile Asp Leu Leu Thr Thr Gly Gln Ala
     50                  55                  60

caa gca gaa aga gca gag ctt act gaa aat att aaa aaa tat aaa tct      240
Gln Ala Glu Arg Ala Glu Leu Thr Glu Asn Ile Lys Lys Tyr Lys Ser
 65                  70                  75                  80

gag ctt gaa gat att gca tac cca tct gct ggc aat aaa gac agt aaa      288
Glu Leu Glu Asp Ile Ala Tyr Pro Ser Ala Gly Asn Lys Asp Ser Lys
                 85                  90                  95

att gca ttt att gag ttc ttc gat tac tct tgt ggt tat tgt aaa atg      336
```

-continued

```
Ile Ala Phe Ile Glu Phe Phe Asp Tyr Ser Cys Gly Tyr Cys Lys Met
            100                 105                 110

atg ttt gaa gat atc aaa caa att ata aaa gat ggt aag gta cgt gtt      384
Met Phe Glu Asp Ile Lys Gln Ile Ile Lys Asp Gly Lys Val Arg Val
        115                 120                 125

att ttt aga gat ttt cca ata ctt ggg gaa tcg tcg tta aag gct gtt      432
Ile Phe Arg Asp Phe Pro Ile Leu Gly Glu Ser Ser Leu Lys Ala Val
    130                 135                 140

aaa gca gca ttg gct gta cat ctt atc aat cca agt aaa tac ttg gac      480
Lys Ala Ala Leu Ala Val His Leu Ile Asn Pro Ser Lys Tyr Leu Asp
145                 150                 155                 160

ttc tat tat gca gca tta aat cat aaa cag cca ttt aat gat gaa tct      528
Phe Tyr Tyr Ala Ala Leu Asn His Lys Gln Pro Phe Asn Asp Glu Ser
                165                 170                 175

ata ctt aat ata gtt aaa tca ctt gaa att tca gaa gag gaa ttt aaa      576
Ile Leu Asn Ile Val Lys Ser Leu Glu Ile Ser Glu Glu Glu Phe Lys
            180                 185                 190

gat tct tta tct aaa aat tct agt act att gat aag atg ata gag tcc      624
Asp Ser Leu Ser Lys Asn Ser Ser Thr Ile Asp Lys Met Ile Glu Ser
        195                 200                 205

act aga aat ctg gct gag aag tta aat atc aga ggt act cct gct ctt      672
Thr Arg Asn Leu Ala Glu Lys Leu Asn Ile Arg Gly Thr Pro Ala Leu
    210                 215                 220

ata ata ggt gat gca ttc att ggg gga gct gca gat tta tca act tta      720
Ile Ile Gly Asp Ala Phe Ile Gly Gly Ala Ala Asp Leu Ser Thr Leu
225                 230                 235                 240

aga agt aaa ata gta gaa cag cag gaa caa taa                          753
Arg Ser Lys Ile Val Glu Gln Gln Glu Gln
                245                 250


<210> SEQ ID NO 32
<211> LENGTH: 250
<212> TYPE: PRT
<213> ORGANISM: Cowdria ruminantium

<400> SEQUENCE: 32

Met Met Ile Arg Ile Phe Leu Leu Leu Gly Leu Val Leu Leu Val Ala
  1               5                  10                  15

Ser Phe Pro Leu Leu Asn Asn Trp Leu Ser Asn His Ser Gly Lys Ser
            20                  25                  30

Thr Thr Leu Asp Lys Asp Ala Val Ile Ser Ile Val Glu Glu Tyr Ile
        35                  40                  45

Thr Asn Tyr Pro Gln Arg Val Ile Asp Leu Leu Thr Thr Gly Gln Ala
     50                  55                  60

Gln Ala Glu Arg Ala Glu Leu Thr Glu Asn Ile Lys Lys Tyr Lys Ser
 65                  70                  75                  80

Glu Leu Glu Asp Ile Ala Tyr Pro Ser Ala Gly Asn Lys Asp Ser Lys
                85                  90                  95

Ile Ala Phe Ile Glu Phe Phe Asp Tyr Ser Cys Gly Tyr Cys Lys Met
            100                 105                 110

Met Phe Glu Asp Ile Lys Gln Ile Ile Lys Asp Gly Lys Val Arg Val
        115                 120                 125

Ile Phe Arg Asp Phe Pro Ile Leu Gly Glu Ser Ser Leu Lys Ala Val
    130                 135                 140

Lys Ala Ala Leu Ala Val His Leu Ile Asn Pro Ser Lys Tyr Leu Asp
145                 150                 155                 160

Phe Tyr Tyr Ala Ala Leu Asn His Lys Gln Pro Phe Asn Asp Glu Ser
                165                 170                 175
```

-continued

```
Ile Leu Asn Ile Val Lys Ser Leu Glu Ile Ser Glu Glu Glu Phe Lys
            180                 185                 190

Asp Ser Leu Ser Lys Asn Ser Ser Thr Ile Asp Lys Met Ile Glu Ser
        195                 200                 205

Thr Arg Asn Leu Ala Glu Lys Leu Asn Ile Arg Gly Thr Pro Ala Leu
    210                 215                 220

Ile Ile Gly Asp Ala Phe Ile Gly Gly Ala Ala Asp Leu Ser Thr Leu
225                 230                 235                 240

Arg Ser Lys Ile Val Glu Gln Gln Glu Gln
                245                 250


<210> SEQ ID NO 33
<211> LENGTH: 450
<212> TYPE: DNA
<213> ORGANISM: Cowdria ruminantium
<220> FEATURE:
<221> NAME/KEY: CDS
<222> LOCATION: (1)..(447)

<400> SEQUENCE: 33

atg cat aga tca aat att att gaa att ttt ata gga ttc cta gtg tta       48
Met His Arg Ser Asn Ile Ile Glu Ile Phe Ile Gly Phe Leu Val Leu
  1               5                  10                  15

gca gga gca ata tct att ggg ata ata gca ttt aac aaa tta cca tat       96
Ala Gly Ala Ile Ser Ile Gly Ile Ile Ala Phe Asn Lys Leu Pro Tyr
             20                  25                  30

aaa aat acc ttg cgt aat tgt tat aca gtt aaa gca ttt ttc tca aat      144
Lys Asn Thr Leu Arg Asn Cys Tyr Thr Val Lys Ala Phe Phe Ser Asn
         35                  40                  45

gta gat ggg ttg gac ata gga gat gaa gta aca ata tca gga gta aaa      192
Val Asp Gly Leu Asp Ile Gly Asp Glu Val Thr Ile Ser Gly Val Lys
     50                  55                  60

ata ggt aca gta act tca ata tca ttg aat gaa agc tat act cct ata      240
Ile Gly Thr Val Thr Ser Ile Ser Leu Asn Glu Ser Tyr Thr Pro Ile
 65                  70                  75                  80

gta aca atg tgc ata cag aaa aat atc tta cta cct tca gat agt tca      288
Val Thr Met Cys Ile Gln Lys Asn Ile Leu Leu Pro Ser Asp Ser Ser
                 85                  90                  95

gca tct ata tta aac agc aat atg tta gga aaa aag cac att gat atc      336
Ala Ser Ile Leu Asn Ser Asn Met Leu Gly Lys Lys His Ile Asp Ile
            100                 105                 110

gaa ctt gga tca gat caa gaa gtc atc gta agt gaa ggt tta ata gaa      384
Glu Leu Gly Ser Asp Gln Glu Val Ile Val Ser Glu Gly Leu Ile Glu
        115                 120                 125

cat aca cat tca gat tta agt ttc aat gca att att gct aaa ata ata      432
His Thr His Ser Asp Leu Ser Phe Asn Ala Ile Ile Ala Lys Ile Ile
    130                 135                 140

gat tca ctt att aag tag                                              450
Asp Ser Leu Ile Lys
145


<210> SEQ ID NO 34
<211> LENGTH: 149
<212> TYPE: PRT
<213> ORGANISM: Cowdria ruminantium

<400> SEQUENCE: 34

Met His Arg Ser Asn Ile Ile Glu Ile Phe Ile Gly Phe Leu Val Leu
  1               5                  10                  15

Ala Gly Ala Ile Ser Ile Gly Ile Ile Ala Phe Asn Lys Leu Pro Tyr
```

-continued

```
                     20                  25                  30

Lys Asn Thr Leu Arg Asn Cys Tyr Thr Val Lys Ala Phe Phe Ser Asn
            35                  40                  45

Val Asp Gly Leu Asp Ile Gly Asp Glu Val Thr Ile Ser Gly Val Lys
    50                  55                  60

Ile Gly Thr Val Thr Ser Ile Ser Leu Asn Glu Ser Tyr Thr Pro Ile
65                  70                  75                  80

Val Thr Met Cys Ile Gln Lys Asn Ile Leu Leu Pro Ser Asp Ser Ser
                85                  90                  95

Ala Ser Ile Leu Asn Ser Asn Met Leu Gly Lys Lys His Ile Asp Ile
            100                 105                 110

Glu Leu Gly Ser Asp Gln Glu Val Ile Val Ser Glu Gly Leu Ile Glu
        115                 120                 125

His Thr His Ser Asp Leu Ser Phe Asn Ala Ile Ile Ala Lys Ile Ile
    130                 135                 140

Asp Ser Leu Ile Lys
145
```